(12) United States Patent
Conero

(10) Patent No.: US 8,818,731 B2
(45) Date of Patent: Aug. 26, 2014

(54) APPARATUS AND METHOD FOR INTERFACING TIME-VARIANT SIGNALS

(75) Inventor: Ronald S. Conero, San Diego, CA (US)

(73) Assignee: Tensys Medical, Inc., San Diego, CA (US)

( * ) Notice: Subject to any disclaimer, the term of this patent is extended or adjusted under 35 U.S.C. 154(b) by 1104 days.

(21) Appl. No.: 12/008,060

(22) Filed: Jan. 7, 2008

(65) Prior Publication Data

US 2008/0109199 A1   May 8, 2008

Related U.S. Application Data

(62) Division of application No. 10/060,646, filed on Jan. 30, 2002, now Pat. No. 7,317,409.

(51) Int. Cl.
*A61B 8/06* (2006.01)

(52) U.S. Cl.
USPC ............................................ 702/19; 600/438

(58) Field of Classification Search
None
See application file for complete search history.

(56) References Cited

U.S. PATENT DOCUMENTS

| | | | |
|---|---|---|---|
| 4,205,386 A | 5/1980 | Ruszala et al. | |
| 4,301,512 A | 11/1981 | Keith et al. | |
| 4,500,933 A | 2/1985 | Chan | |
| 4,705,047 A | 11/1987 | Bailey | |
| 4,736,322 A | 4/1988 | Clifford | |
| 4,760,730 A | 8/1988 | Frank et al. | |
| 5,016,631 A | 5/1991 | Hogrefe | |
| 5,042,307 A | 8/1991 | Kato | |
| 5,101,828 A | 4/1992 | Welkowitz et al. | |
| 5,124,661 A | 6/1992 | Zelin et al. | |
| 5,135,002 A | 8/1992 | Kirchner et al. | |
| 5,146,401 A | 9/1992 | Bansal et al. | |
| 5,193,547 A | 3/1993 | Evans, II et al. | |
| 5,264,958 A | 11/1993 | Johnson | |
| 5,325,865 A | 7/1994 | Beckman et al. | |
| 5,533,511 A | 7/1996 | Kaspari et al. | |
| 5,568,815 A | 10/1996 | Raynes et al. | |
| 5,616,850 A * | 4/1997 | Sage | 73/23.31 |
| 5,623,925 A | 4/1997 | Swenson et al. | |
| 6,141,572 A | 10/2000 | Haas | |
| 6,443,906 B1 | 9/2002 | Ting et al. | |
| 6,471,646 B1 | 10/2002 | Thede | |
| 6,471,655 B1 | 10/2002 | Baura | |
| 6,514,211 B1 | 2/2003 | Baura | |
| 6,554,774 B1 | 4/2003 | Miele | |
| 6,676,600 B1 * | 1/2004 | Conero et al. | 600/438 |
| 2002/0062086 A1 | 5/2002 | Miele et al. | |
| 2003/0004421 A1 | 1/2003 | Ting et al. | |

FOREIGN PATENT DOCUMENTS

WO    WO0117425    * 3/2001 ................ 600/438

OTHER PUBLICATIONS

JAMECO Electronics catalog. pp. 1-14. Copyright 1996 by the National Semiconductor Corporation (USA). http://www.national.com.

\* cited by examiner

*Primary Examiner* — Anna Skibinsky
(74) *Attorney, Agent, or Firm* — Gazdzinski & Associates, PC

(57) ABSTRACT

An improved apparatus and method for interfacing a time variant waveform between two hardware environments. In one aspect, the invention comprises a circuit for accurately simulating the output of one or more types of sensing device (e.g., passive bridge pressure transducer) for use with a plurality of different monitoring and/or analysis devices, thereby obviating the need for specialized interface circuitry adapted to each different monitor/analyzer. In one exemplary embodiment, the sensing device comprises a non-invasive blood pressure monitor (NIBPM), which universally interfaces with prior art patient monitors via the interface circuit of the invention. In a second aspect of the invention, an improved NIBPM device incorporating the interface circuit is disclosed. An improved disconnect circuit adapted to sense the status of the electrical connection between the sensing device and monitor is also described.

15 Claims, 18 Drawing Sheets

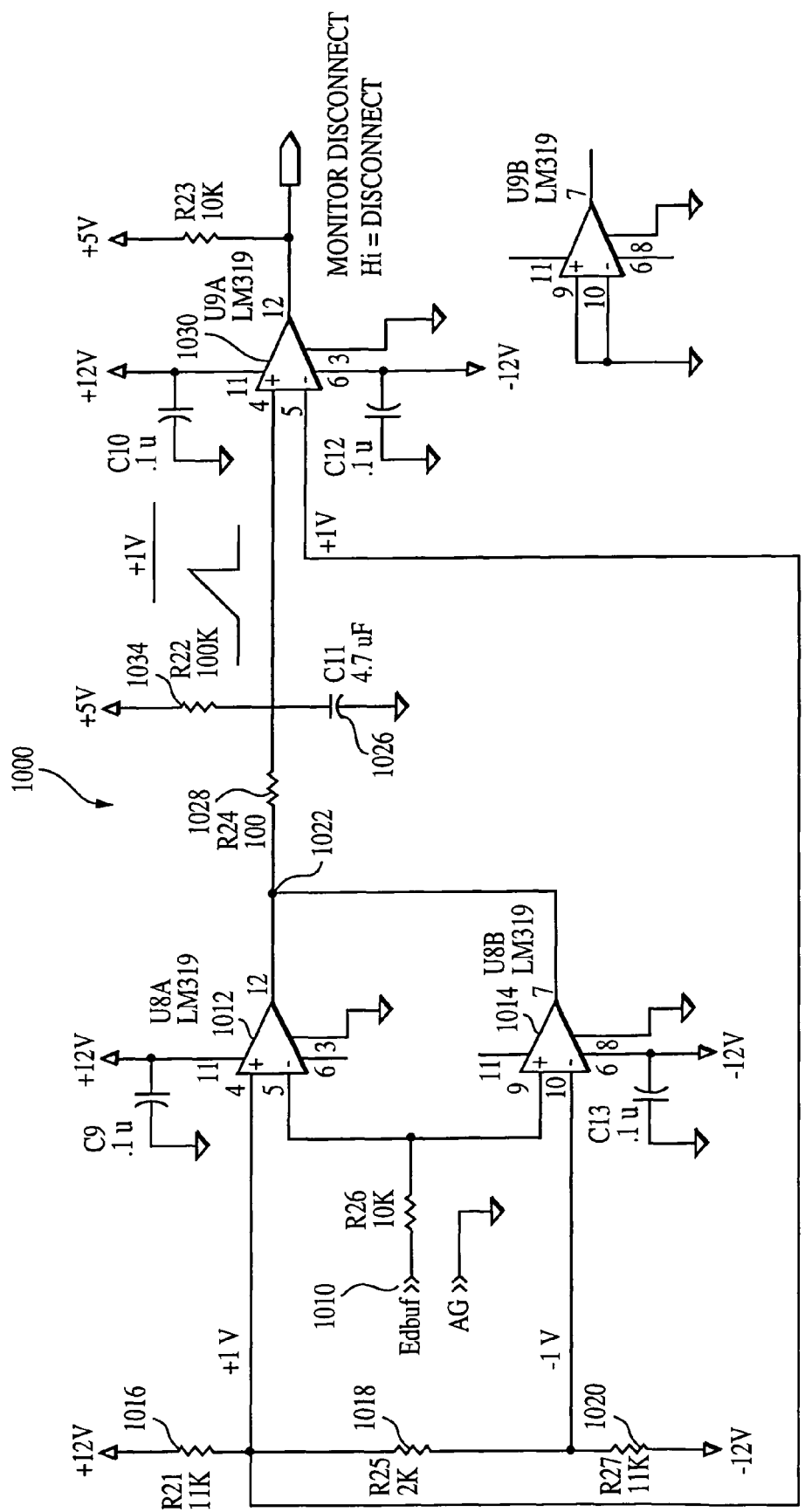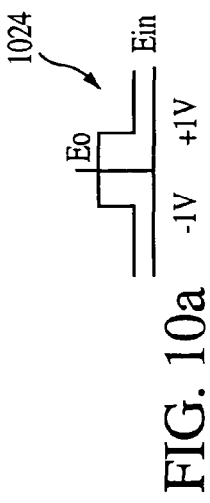
FIG. 10a
FIG. 10

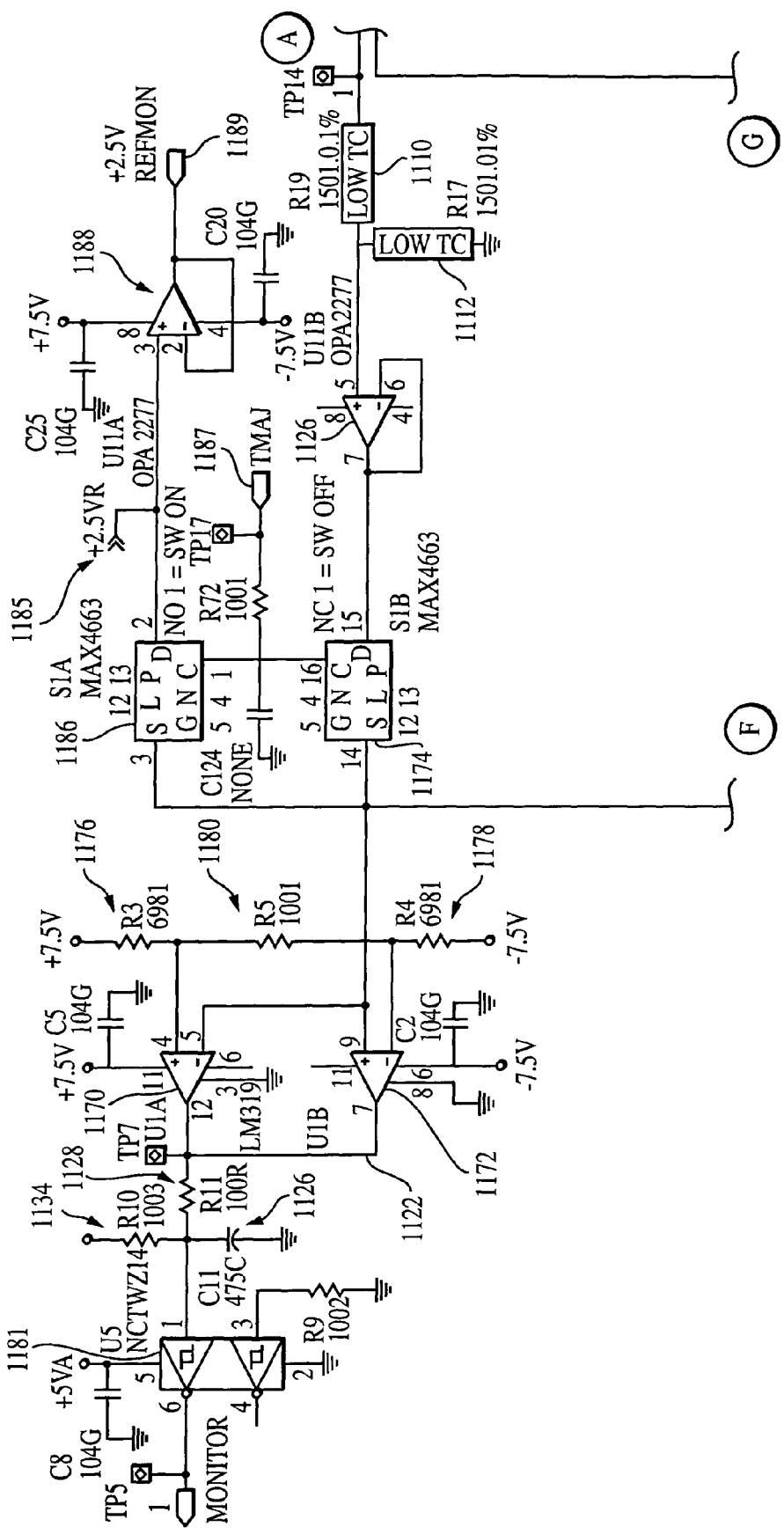
FIG. 11 (PART 1 OF 4)

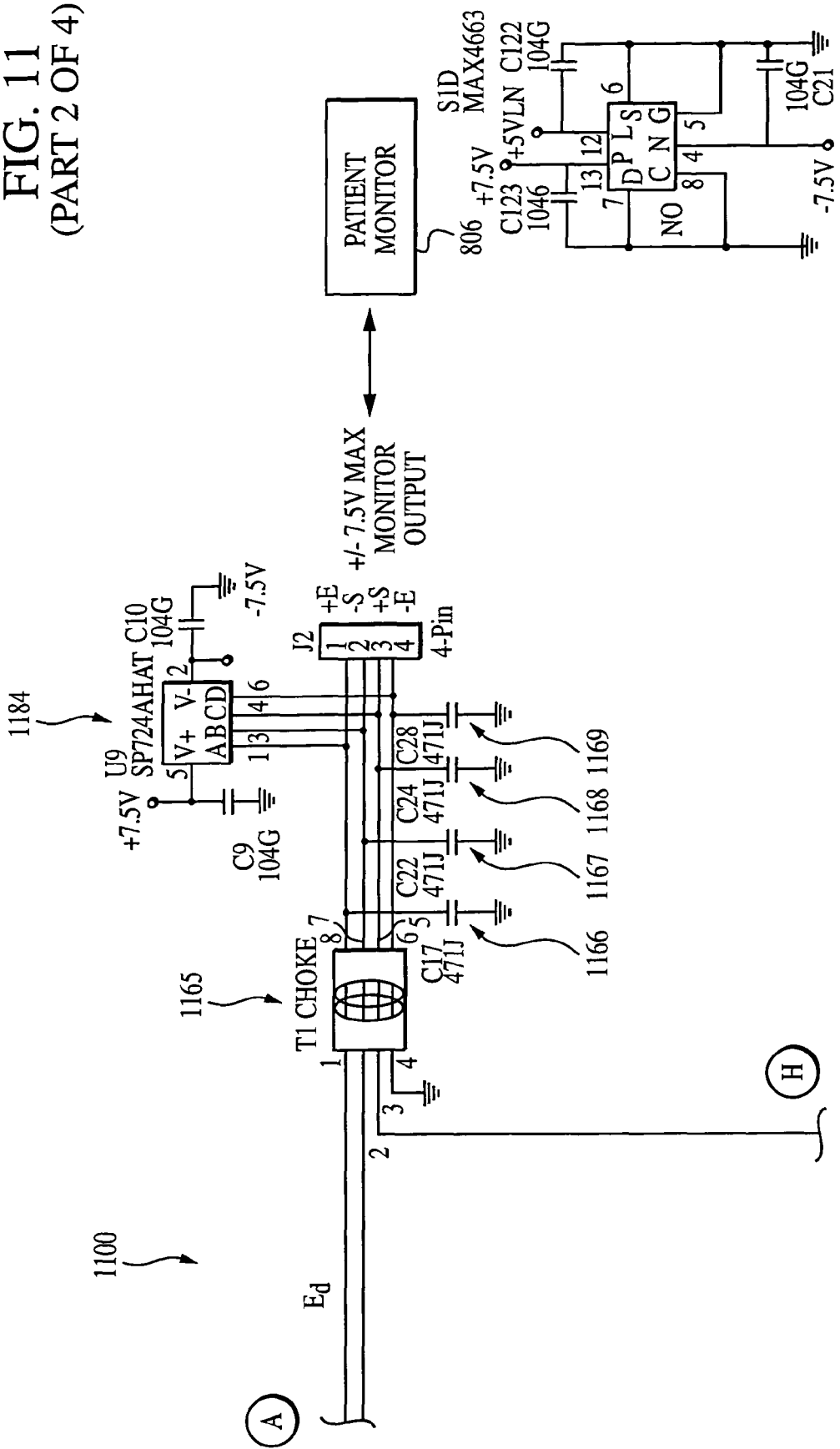
FIG. 11 (PART 2 OF 4)

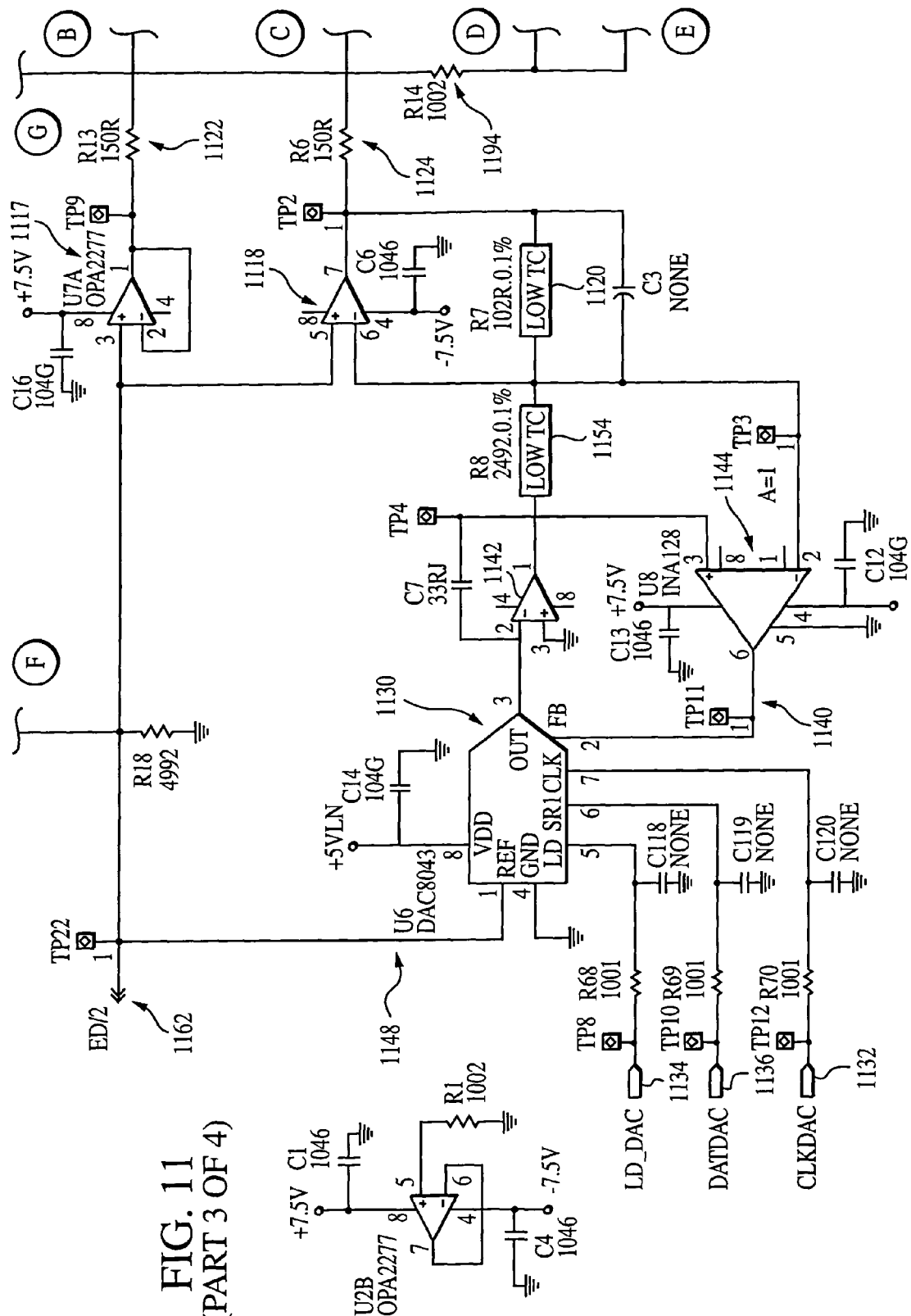
FIG. 11 (PART 3 OF 4)

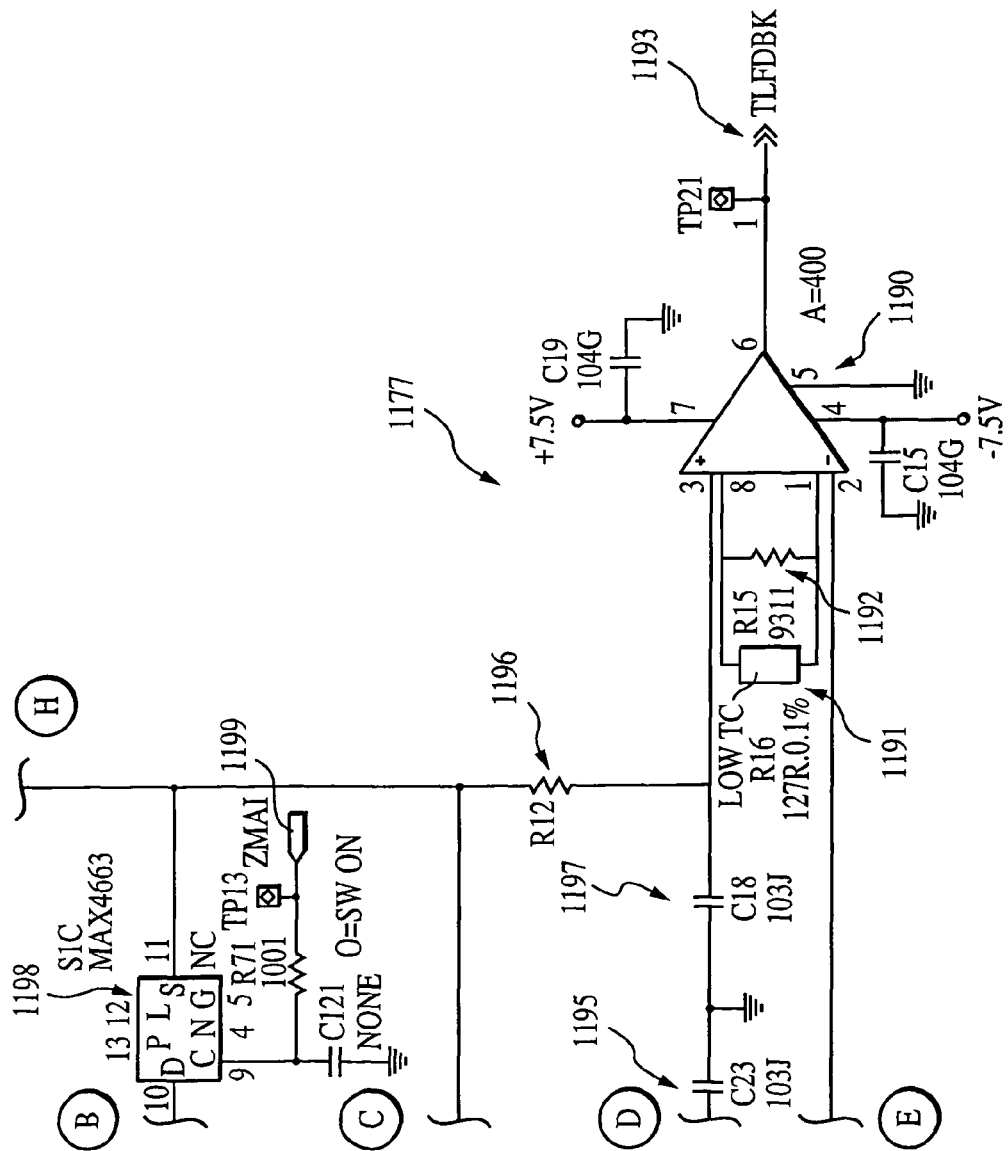
FIG. 11 (PART 4 OF 4)

APPARATUS AND METHOD FOR INTERFACING TIME-VARIANT SIGNALS

The present invention is a divisional of U.S. application Ser. No. 10/060,646 filed Jan. 30, 2002, of the same title, which issues as U.S. Pat. No. 7,317,409 on Jan 8, 2008.

BACKGROUND OF THE INVENTION

1. Field of the Invention

This invention relates generally to apparatus and methods for interfacing time-variant signals, and specifically to the conditioning/simulation of waveforms (such as, for example, blood pressure waveforms) on monitoring equipment.

2. Description of Related Technology

Slowly time-variant waveforms or signals have broad application in many fields, including industry, research, and medicine. Within the medical field, one application of particular interest relates to the monitoring of arterial blood pressure within living subjects (such as human beings and canines). As part of so-called "invasive" arterial blood pressure monitoring, a disposable pressure transducer is commonly utilized to measure the blood pressure of the subject via an invasive arterial line that infuses normal saline at a "KVO" rate into an appropriate blood vessel. KVO (or "keep vein open") refers to the minimum flow rate required to keep an IV needle from clotting off in the vein. The disposable pressure transducer (DPT) is a passive resistive bridge implemented typically from silicon strain beam technology. The DPT electrically interfaces to a patient monitor available from any number of different vendors such as Hewlett Packard/Agilent/Philips, General Electric/Marquette, Datex-Ohmeda, Datascope/Fakuda-Denshi, Welch Allyn/Protocol, Space Labs, Criticare, Critikon, and Valley Medical, as well as others. The patient monitor supplies the excitation signal to energize the bridge circuit of the DPT, and also provides the signal conditioning of the output derived from the DPT in order to display the subject's blood pressure waveform on the display device of the patient monitor.

The various monitors described above utilize varying methods to energize the bridge and recover the output signal. In one simple scheme (shown as FIG. 1), the bridge 101 of the DPT 100 is driven by a constant direct current (DC) voltage source 102. The value of the DC voltage produced by the source 102 can be any value between 1V and 10V, but is typically set at 5V. This voltage value minimizes the self-heating effect that occurs when resistors R1 104, R2 106, R3 108, R4 110, R5 112, and R6 114 dissipate power. This power dissipation changes the temperature of the bridge sensor resistors R3 108, R4 110, R5 112, and R6 114, and causes their electrical resistance values to change. This change in resistance causes an error in the output of the bridge 101 which is not desired. Usually the manufacturer of the DPT will add additional resistors (not shown) to compensate for such temperature effects, and to calibrate the output of the DPT to a particular value (such as 5 uV/V/mnHg). None-the-less, minimizing the self-heating of the components limits the magnitude of the error, since such electrical compensation is never perfect.

As shown in FIG. 1, the drive signal to the DPT 100 is applied across the +E 120 and −E 122 terminals. Resistors R1 104 and R2 106 limit bridge current, and provide temperature compensation for span. When pressure is applied to the transducer, the geometry of the silicon strain beam is arranged so that resistors R3 108 and R6 114 decrease in value, and the values of resistors R4 110 and R5 112 increase in value by the same amount. This change is typically on the order of 1% of the resistor's resistance value, and is commonly referred to as "Delta R" or ΔR. In a typical configuration, resistors R3 108, R4 110, R5 112, and R6 114 all have the same nominal value referred to as $R_b$. Resistors R1 and R2 are usually chosen to have equal resistance so that the nominal voltage at terminals +S 130 and −S 132 will be equal to one-half of the drive voltage $E_d$. For these conditions, the output impedance of the bridge 101 will be $R_b$, and the input impedance will be given by Eqn. 1:

$$Zin = R1 + R2 + Rb \qquad \text{(Eqn. 1)}$$

Typical values for Zin and Zout ($R_b$) are 3K ohms and 300 ohms, respectively. Given these definitions, it can be readily demonstrated that the bridge output voltage across terminals +S 130 and −S 132 can be described by Eqn. 2 as follows:

$$Es = +S - (-S) = Ed \times \frac{dR}{Zin} \qquad \text{(Eqn. 2)}$$

Derivation of Eqn. 2 is conducted by analyzing an equivalent balanced bridge configuration 200 (FIG. 2) based on the following six assumptions: (i) Resistor R1 202=R2 202; (ii) Resistors R3 204, R4 206, R5 208, and R6 210 are all equal in resistance when the bridge 200 is in balance, and are equal to $R_b$; (iii) when the bridge unbalances, resistors R3, R4, R5, and R6 all change by an equal amount (dR) as shown in FIG. 3; (iv) the load across terminals +S 230 and −S 232 is an infinite differential impedance; (v) there are no loads between +S and +E or −E; and (vi) there are no loads between −S and +E or −E.

When the bridge in FIG. 2 is in balance, the resistance between terminal 1 240 and terminal 2 242 is given by $R_b$ (i.e., 2×Rb placed in parallel with 2×Rb yields an effective impedance of $R_b$). In the unbalanced configuration of FIG. 3, the resistance between terminal 1 340 and terminal 2 342 is also given by $R_b$, since the quantity (R3+R4+dR−dR)=2$R_b$, which, when placed in parallel with (R5+R6+dR−dR)=2$R_b$, yields an effective impedance of $R_b$. Similarly, the bridge output impedance Zout=$R_b$.

The unbalanced circuit of FIG. 3 can be simplified to an equivalent circuit 400 shown as FIG. 4 herein. The input impedance seen by the excitation source $E_d$ is therefore given by Eqn. 3:

$$Z_{in} = R1 + R2 + Rb \qquad \text{(Eqn. 3)}$$

The relationship between Eb (i.e., the equivalent voltage across the bridge) and the excitation voltage $E_d$ is given by Eqn. 4:

$$Eb = Ed \times \left[ \frac{Rb}{R1 + R2 + Rb} \right] \qquad \text{(Eqn. 4)}$$

Note, however, that (R1+R2+Rb)=$Z_{in}$. Hence, Eb can be represented as shown in Eqn. 5:

$$Eb = Ed \times \left[ \frac{Rb}{Zin} \right] \qquad \text{(Eqn. 5)}$$

The bridge may be analyzed alone, since the voltage $E_b$ across the bridge is constant (and hence $R_b$ is constant). This unbalanced circuit equivalent 500 is shown in FIG. 5 herein. The voltage at node +S 502 is given by Eqn. 6:

$$E(+S) = Eb \times \left[\frac{Rb + dR}{Rb + dR + Rb - dR}\right] \quad \text{(Eqn. 6)}$$

$$= E(+S) = Eb \times \left[\frac{Rb + dR}{2 \times Rb}\right]$$

$$= E(+S) = Eb \times \left[\frac{1}{2} + \frac{dR}{2 \times Rb}\right].$$

A similar expression can be developed for the voltage at node −S 504 (Eqn. 7):

$$E(-S) = Eb \times \left[\frac{1}{2} - \frac{dR}{2 \times Rb}\right] \quad \text{(Eqn. 7)}$$

The differential output E(s) is simply E(+s)−E(−s), as follows:

$$E(S) = Eb \times \left\{\left[\frac{1}{2} + \frac{dR}{2 \times Rb}\right] - \left[\frac{1}{2} - \frac{dR}{2 \times Rb}\right]\right\} = \quad \text{(Eqn. 8)}$$

$$E(S) = Eb \times \left[\frac{dR}{Rb}\right]$$

Finally, substituting the result of Eqn. 5 into Eqn. 8 yields Eqn. 2 above:

$$E(s) = Ed \times \left[\frac{dR}{Zin}\right]$$

In order for all DPT's to function similarly, they are typically calibrated during manufacture to a standard sensitivity of 5 uV/V/mmHg. This means that for an applied pressure of 100 mmHg, and a drive voltage ($E_d$) of 5V, the output $E_s$ will be 2.5 mV. This requires that the resistance difference (dR) be 1.5 ohms, according to Eqn. 2 above. For a Zin of 3 kohms, the full-scale pressure specification for such DPTs is 300 mmHg, which would require a resistance difference (dR) value of 4.5 ohms, and yield an output voltage of 7.5 mV.

It can be shown that the differential resistance dR is a function of pressure:

$$dR = Ks \times Zin \times P \quad \text{(Eqn. 9)}$$

where:
$K_s$=scaling factor of 5 uV/V/mmHg, and
P=sensed pressure.
Substituting this result into Eqn. 2 results in the transfer function for the bridge, Eqn. 10:

$$Es = Ed \times Ks \times P \quad \text{(Eqn. 10)}$$

Note that the output voltage Es is a function of both pressure (P), the input variable, and the drive voltage (Ed) provided by the monitor.

For the 5 VDC drive condition, the signal processing of the output is typically quite limited in scope; e.g., amplifying the bridge output with an instrumentation amplifier, and filtering the output with a 2-pole low pass filter whose cutoff frequency is above any frequency components of interest in the blood pressure signal. A typical valve for such filter cutoff frequency is 45 Hz.

When a user wishes to supply the monitor with and display a waveform other than that derived from the aforementioned DPT (such as that from a digital non-invasive blood pressure monitor such as that manufactured by the Assignee hereof), the DPT must be disconnected from the monitor, and the new signal source electrically substituted. For the case of a fixed DC drive voltage of 5V, a circuit may be readily fashioned to interface the new (e.g. digital) signal source to the patient monitor, such as that shown in FIG. 6.

As illustrated in FIG. 6, resistor R1 602 of the interface circuit 600 allows the patient monitor detect the 3 Kohm impedance value (Zin) it normally sees when using the DPT. Additionally, resistors R2 606 and R3 608 set the differential output impedance ($Z_{out}$) to 300 ohms. The output of node S+610 is biased to +2.5 V by reference amplifier U1 616, and amplifiers U2 618 and U3 620 (and their associated components) set the −S output according to Eqn. 11:

$$-S = 2.506 - 0.0025 \times Ein \quad \text{(Eqn. 11)}$$

The differential output between +S and −S is given by Eqn. 12:

$$Es = -0.006 + 0.0025 \times Ein \quad \text{(Eqn. 12)}$$

The fixed offset of −6 mV (for the exemplary circuit of FIG. 6) can be "zeroed out" or cancelled by most patient monitors, leaving the output voltage $E_s$ a function of the input voltage, and scaled such that a 1V input equals 100 mmHg. An alternative to nulling out the −6 mV with the monitor is to add a zero adjustment to amplifier U2 618.

While the circuit 600 of FIG. 6 (or any other similar circuit) works generally for any monitor that has a fixed +5V DC constant voltage excitation, it has significant shortcomings when one attempts to drive the many different types of patient monitors presently available. Many such patient monitors do not use constant +5V excitation, but rather use bipolar sine wave drive, or even pulse drive as a carrier between 2 KHz and 5 KHz, which is modulated by the pressure signal. These monitors use an AC drive to reduce bridge offset effects, and cancel noise. Furthermore, they require a synchronous demodulator as part of their signal conditioning circuitry, in order to recover the blood pressure modulation signal.

Therefore, in order to drive these monitors with a non-DPT device such as the aforementioned digital NIBPM, a circuit is needed that mimics the electrical profile and operation of a passive transducer bridge. The transfer function of such circuit must be effectively identical to that of the passive bridge, and the input and output impedances must match those of the passive bridge as well. The sensitivity factor of 5 uV/V/mmHg previously described (or any corresponding value for the selected monitor) must also be maintained. The circuit must function with any type of excitation source including constant voltage drive of either polarity, constant current drive of either direction, and any AC voltage or current drive of any waveshape, duty cycle, and DC offset with a frequency of 1 KHz to 10 KHz.

Based on the foregoing, what is needed is an improved apparatus and method for interfacing sensing devices producing time variant waveforms (such as for example the systolic, diastolic, and/or average blood pressure waveforms of a living subject) with monitoring devices. Such apparatus and method would ideally (i) be readily adapted to a variety of different configurations of monitoring or display devices, (ii) have a wide dynamic range; (iii) be able to operate on binary digital input (versus requiring conversion to analog first); (iv) maintain the desired sensitivity factor; (v) function with any type of excitation source including constant voltage drive of either polarity; (vi) function with a constant current drive of either direction, and (vii) function with any AC voltage or current drive of any waveshape, duty cycle, and DC offset. Furthermore, such circuit would optimally be electrically isolable from the monitor, be stable and have minimal error or drift through its simulation range, and include provision for the detecting when the monitoring device was electrically connected thereto.

SUMMARY OF THE INVENTION

The present invention satisfies the aforementioned needs by providing improved apparatus and methods for interfacing time-variant signals between different hardware environments, including the blood pressure waveforms obtained from a living subject.

In a first aspect of the invention, an apparatus useful for interfacing a time-variant signal between two hardware environments is disclosed. In one exemplary embodiment, the apparatus is adapted to accurately simulate one or more types of passive bridge pressure transducer. The interface apparatus is configured to simulate any signal that the pressure transducer could produce, including waveforms having frequency ranging from direct current (i.e., 0 Hz) up through several hundred Hertz. In one variant of this apparatus, a circuit adapted to simulate the one or more blood pressure waveforms as would be produced by a disposable passive bridge pressure transducer (DPT) is provided. The circuit comprises a digital-to-analog converter (DAC) receiving digital inputs from the associated blood pressure sensing and processing apparatus (e.g., a pressure-based tonometric systems, or combined pressure/Doppler-based ultrasonic system, and its attendant signal processing), which are then conditioned using a linear transfer function which replicates that of a DPT bridge device. The circuit uses the excitation signal from the patient monitor as the reference, and advantageously requires no analog signal synthesis; accordingly, no dependency upon voltage references or errors inherent therein is present. The circuit is further "universal" in nature, being adapted to interface with essentially any different configuration of monitoring device, regardless of the type of excitation used by that monitoring device for the DPT, or type of output signal conditioning applied. The circuit also comprises an adjustable scale factor, such factor being based on the adjustment of the ratio of two resistance values, and inherently has very low drift, thereby further enhancing accuracy.

In a second aspect of the invention, a method for simulating a time-variant output signal from a first device using a second device is disclosed. The method generally comprises providing the second device; providing an excitation voltage to the second device; generating a digital representation of a time-variant waveform using the second device; applying a transfer function to the digital representation, the transfer function being substantially similar to that for the first device; and generating an output signal based at least in part on the digital representation and the transfer function, the output signal being substantially similar to that produced by the first device. In one exemplary embodiment, the first device comprises a passive bridge element, the time-variant waveform comprises a blood pressure waveform obtained from a living subject, and the second device comprises a non-invasive blood pressure monitor (NIBPM). The NIBPM is connected to a conventional monitoring device typically used with prior art passive bridge DPT devices, the presence of the NIBPM being detected through the presence of a specified impedance (or alternatively, a voltage at a predetermined terminal of the monitor). The method further comprises buffering the excitation signal provided to the NIBPM, and disposing the DAC in feedback loop arrangement whereby the internal current thereof flows is a function of a predetermined parameter (e.g., the DAC count, N).

In a third aspect of the invention, an improved disconnect circuit for detecting when a monitoring device (such as a patient monitor) is disconnected from its sensing apparatus (e.g., Doppler blood pressure sensor) is disclosed. The disconnect circuit detects the presence of a monitor by detecting a signal associated with the monitor; e.g., the drive signal the monitor uses to excite the passive bridge normally used with the monitor. Rather than evaluating this signal directly, the disconnect circuit of the present invention evaluates a buffered version of the signal. In one exemplary embodiment, the disconnect circuit is physically disposed in the sensing apparatus. A window comparator transfer function is used for detection; thus, as long as some part of the drive signal waveform exceeds a predetermined signal magnitude, the output of the window comparator will be held in a predetermined state. This approach ensures that any signal of any shape or duty cycle will be detected by the circuit. A comparatively long time constant is also used to avoid zero-crossing waveforms or other momentary voltage dips from inducing unwanted or spurious artifacts.

In a fourth aspect of the invention, an improved apparatus for non-invasively measuring the blood pressure of a living subject is disclosed. In one exemplary embodiment, the apparatus comprises (i) an ultrasonic Doppler-based system adapted to measure the hemodynamic properties associated with the subject, such as blood kinetic energy or velocity, and determine arterial blood pressure there from, and develop at least one binary digital signal related thereto; and (ii) the interface circuit previously described. The hemodynamic parameter measurement system comprises a signal processor operatively coupled to an ultrasonic transducer and a pressure transducer, and an applanation device adapted to control applanation pressure applied to the transducer(s). The signal processor (and associated algorithms) generate a calibration function and determine blood pressure based on the measured data and the derived calibration function. The blood pressure measurement data is fed to the interface circuit, which conditions the signal so as to allow data communication with a monitor. The interface circuit is adapted to communicate data with literally any type of monitor device (regardless of manufacturer), and hence the apparatus may advantageously be used to non-invasively measure blood pressure from a subject irrespective of the in situ monitoring equipment available. In a second embodiment, the ultrasonic system measures various parameters associated with the blood vessel of the subject, and determines blood pressure based at least in part by calculating time frequency distributions for the collected data. In yet another embodiment, the apparatus is configured with a wireless (e.g., radio frequency) data link such that digital data representative of the subject's blood pressure is transmitted to the interface circuit disposed proximate to the patient monitor, thereby obviating the need for electrical cords.

In a fifth aspect of the invention, an improved apparatus for monitoring the blood pressure of a living subject is disclosed. The apparatus generally comprises a non-invasive blood pressure monitoring (NIBPM) device coupled via the aforementioned simulation circuit to a monitor system, the latter adapted to monitor and optionally analyze, display, and record blood pressure waveform data (and other relevant data) relating to a given subject. In one exemplary embodiment, the NIBPM apparatus comprises an ultrasonic Doppler-based system adapted to measure the hemodynamic properties associated with the subject, such as blood kinetic energy or velocity, and determine arterial blood pressure there from, and develop at least one binary digital signal related thereto. The interface circuit previously described herein is used to provide hardware interface between the NIBPM and the monitor. The monitor comprises a device adapted to receive the analog signal from the NIBPM via the interface circuit, and analyze the data within the processing of the monitor in order to derive (and display) the resultant measured value of blood pressure.

In a sixth aspect of the invention, an improved method of providing treatment to a subject using the aforementioned apparatus and method is disclosed. The method generally comprises: obtaining data from the subject using a sensing device; generating a first signal based at least in part on the obtained data; conditioning the first signal using a conditioning circuit to produce a second signal; providing the second signal to a monitoring device, the latter producing a representation of a desired parameter, and providing treatment to the subject based on the parametric representation. In one exemplary embodiment, the data obtained from the subject comprises arterial hemodynamic data (e.g., pressure, velocity, kinetic energy) obtained from the radial artery of the human being, and the sensing device comprises the aforementioned ultrasonic NIBPM system with associated interface circuit. The digital representation of arterial blood pressure generated by the NIBPM system is input to the interface circuit, which conditions the signal for "universal" use by any monitoring system. The selected monitoring system takes the conditioned blood pressure signal and displays the waveform or other representation (such as digital values of mean, systolic, and diastolic pressures) for use by the care-giver. The care-giver then prescribes a course of treatment (such as the administration pharmaceuticals, or additional monitoring) based on the displayed information.

BRIEF DESCRIPTION OF THE DRAWINGS

FIG. 10 is a schematic diagram of one exemplary embodiment of the disconnect circuit optionally used in conjunction with the interface circuit of FIG. 8 or 9.

FIG. 10*a* is a graph illustrating the operation of the windowing function associated with the comparator of the disconnect circuit of FIG. 10.

FIG. 11 is a schematic diagram of a third embodiment of the interface circuit of the invention, also comprising self-test functionality.

DETAILED DESCRIPTION OF THE INVENTION

Reference is now made to the drawings wherein like numerals refer to like parts throughout.

It is noted that while the invention is described herein primarily in terms of a method and apparatus for assessing the hemodynamic parameters of the circulatory system via the radial artery (i.e., wrist) of a human subject, the invention may also be embodied or adapted to monitor such parameters at other locations on the human body, as well as monitoring these parameters on other warm-blooded species. Furthermore, in the broader sense, the invention may be readily applied outside the medical field, such as for example to pressure monitoring devices in fluidic systems, where it is desirable to have universal functionality or interconnection between the sensing device and an associated monitoring device. It can be used to drive the signal processing circuits for any bridge-type transducer monitor that processes time-variant signals (e.g., 200 Hz or less). All such applications, adaptations and alternate embodiments are considered to fall within the scope of the claims appended hereto.

As used herein, the term "non-invasive blood pressure monitor" or "NIBPM" refers to any apparatus adapted to measure or estimate the blood pressure within a blood vessel of a living subject in either partially or completely non-invasive manner, regardless of method used.

Figure 1:
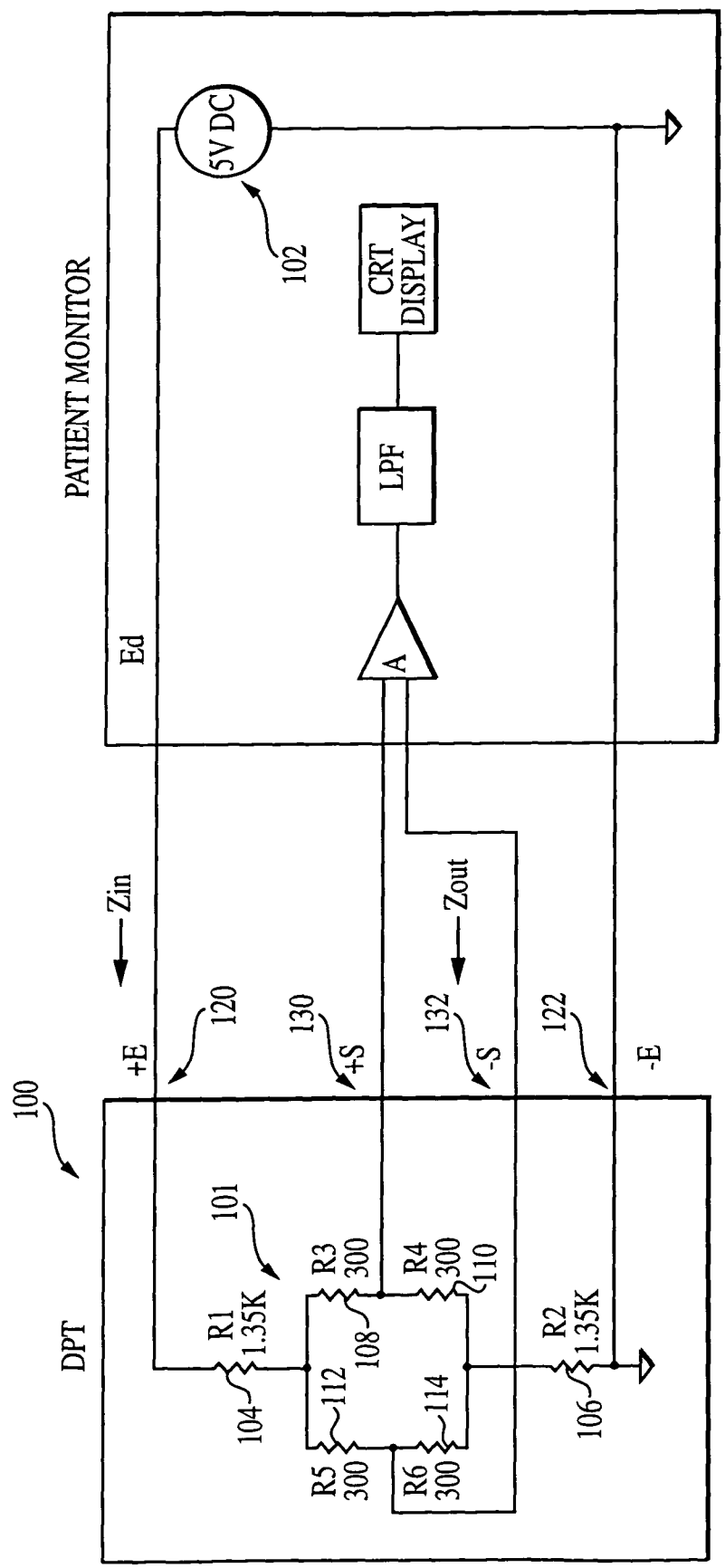
FIG. 1 is a schematic diagram of an exemplary prior art circuit used to energize and recover the output signal from a passive resistance bridge used in a disposable pressure transducer (DPT).
Figure 2:
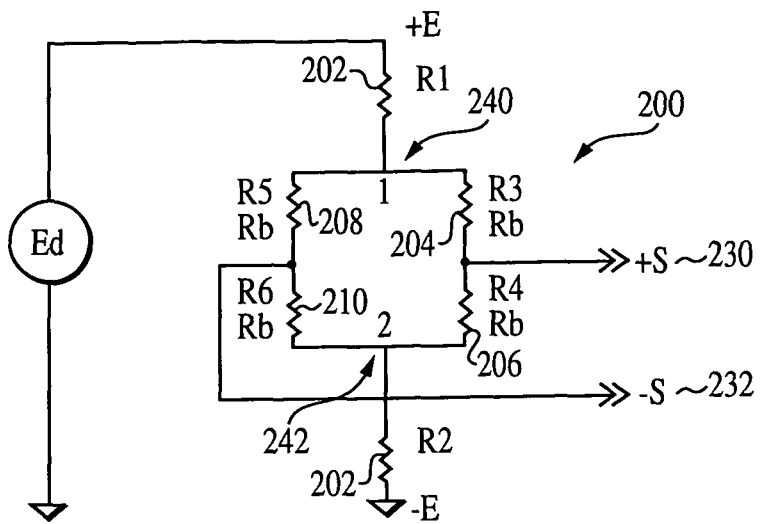
FIG. 2 is a schematic diagram of a balanced bridge circuit which is electrically equivalent to that of FIG. 1.
Figure 3:
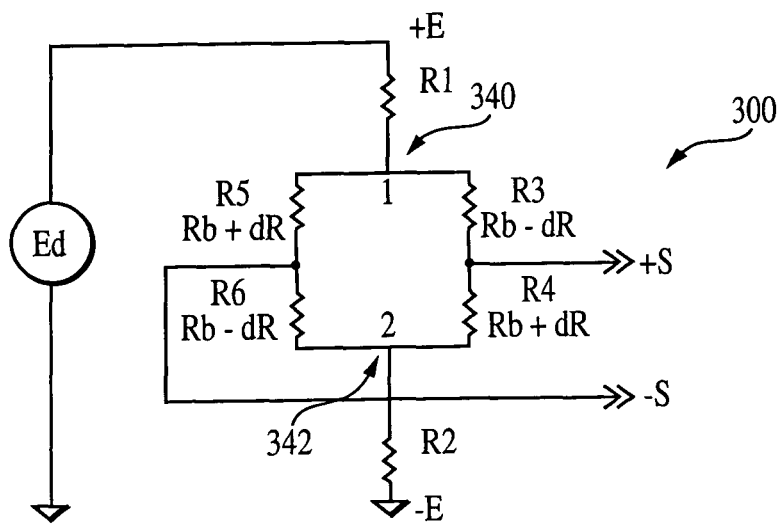
FIG. 3 is a schematic diagram of the equivalent circuit of FIG. 2, except in an unbalanced condition.
Figure 4:
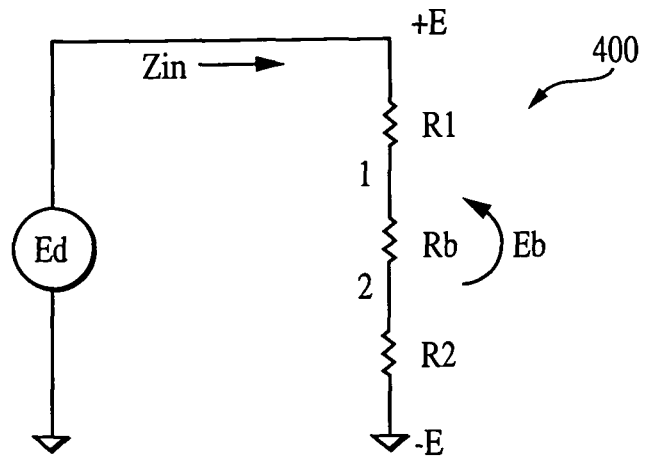
FIG. 4 is a schematic diagram of an unbalanced bridge circuit which is electrically equivalent to that of FIG. 3.
Figure 5:
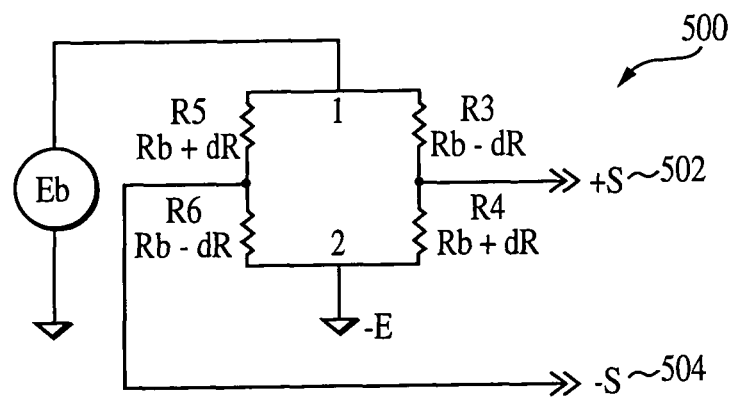
FIG. 5 is a schematic diagram of the unbalanced bridge circuit of FIG. 4, excerpt wherein the circuit is simplified to reflect the bridge resistance $R_b$ alone.
Figure 6:
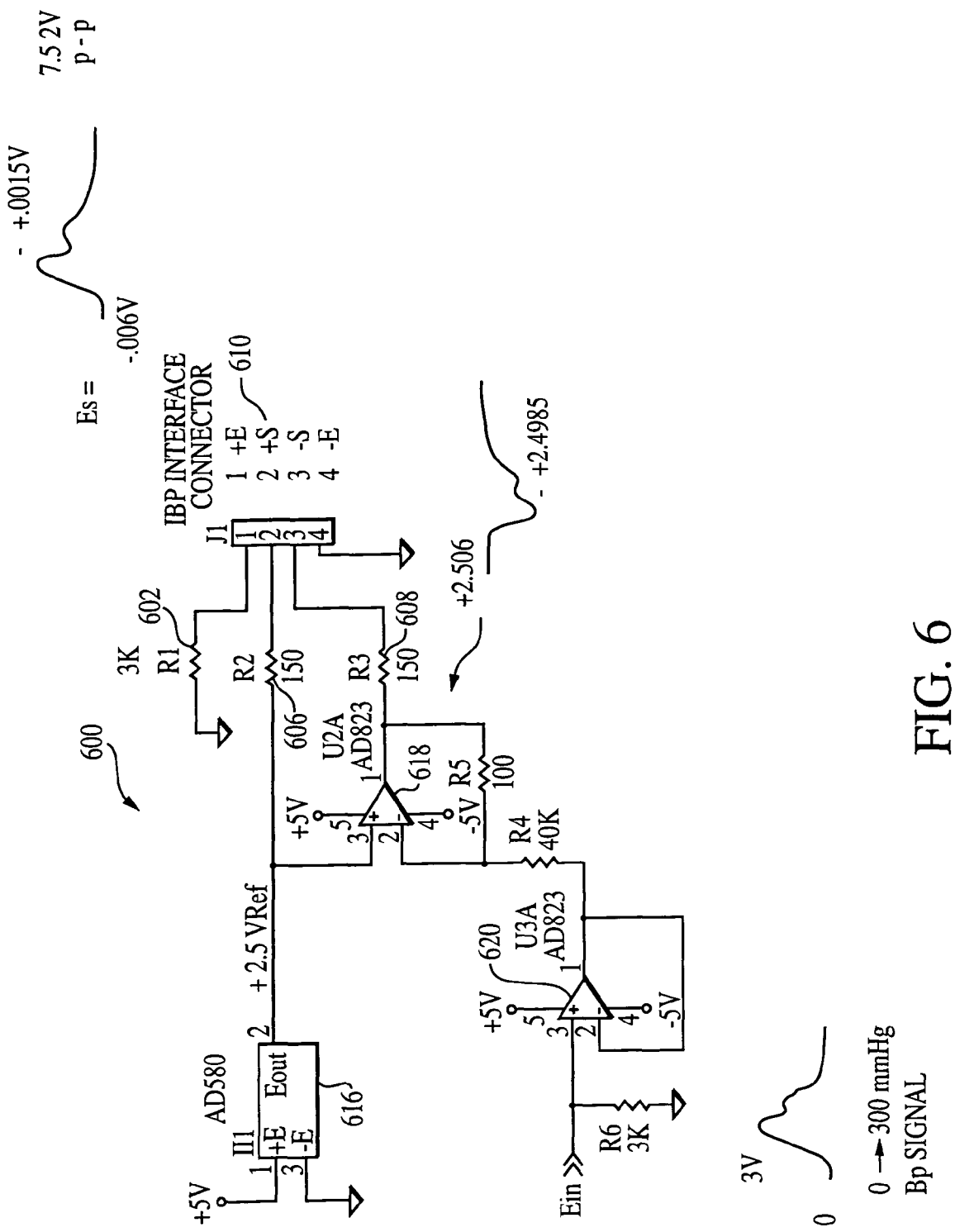
FIG. 6 is a schematic diagram of an exemplary prior art circuit adapted to interface a non-DPT signal source to a fixed DC drive voltage patient monitor.
Figure 7:
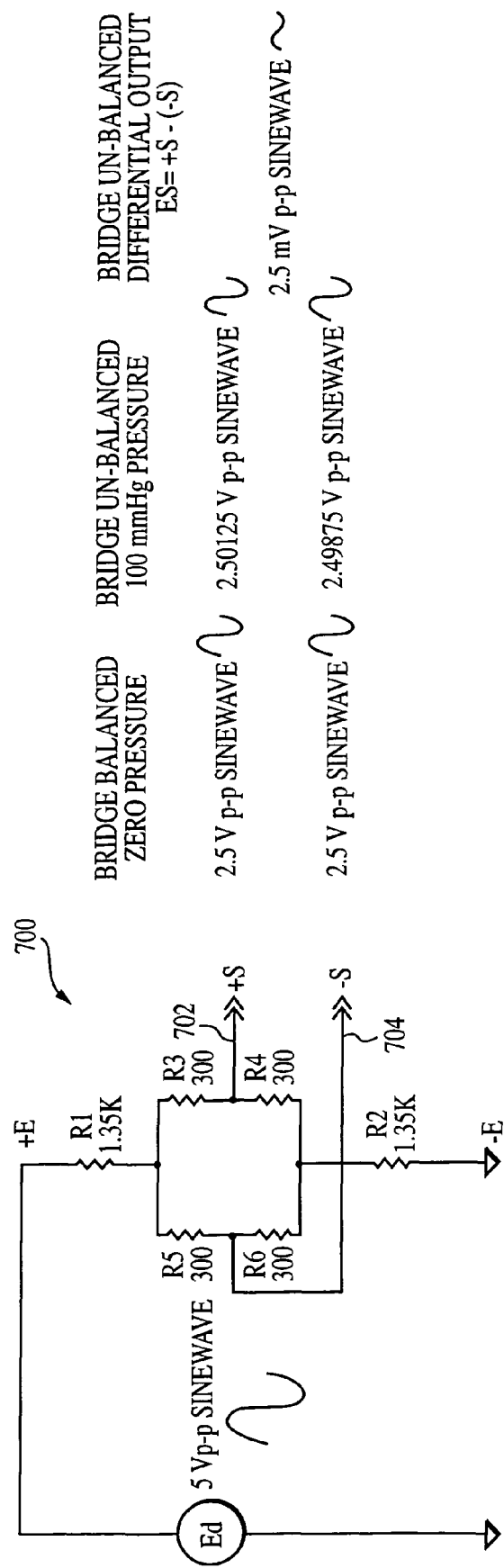
FIG. 7 is a schematic diagram of an exemplary prior art passive bridge device illustrating the response thereof to a sine wave excitation signal applied at the drive input of the bridge.

Referring now to FIG. 7, the response of an exemplary prior art passive bridge device to a sine wave excitation applied at the drive input of the bridge is analyzed. Assuming perfect matching in the bridge 700, the outputs +S 702 and −S 704 are also sine waves in phase with the excitation voltage, but at one-half the amplitude of the drive voltage. If the bridge 700 senses an applied pressure (for example, of 100 mmHg), its resistance is altered by an amount equal to delta R, and the output sine wave amplitudes at +S 702 and −S 704 change by 1.25 mV each, but in different directions. The differential output of the exemplary bridge 700 of FIG. 7 will be a sine wave in phase with the drive, with an amplitude of 2.5 mV. The amplitude of this differential signal will follow the blood pressure waveform applied to the device, which varies at a much lower frequency. Specifically, the period of the blood pressure signal can range between about 1.7 sec (35 beats/minute) to 0.25 sec (240 beats/minute). The blood pressure waveform can be obtained by synchronously demodulating the output signal with the drive excitation sine wave.

Recalling the transfer function of the passive bridge, Es=Ed×Ks×P (Eqn. 10 above), it can be seen that the output of any interface circuit used to universally mimic or "simulate" the passive bridge must be a function of both the pressure signal P, and also a function of the drive excitation source $E_d$. Further, the transfer function shows that a multiplication must take place between the variables for the interface circuit to function the same as the passive bridge. Since Ed can be bipolar, at least 2 quadrant multiplication is implied.

Since the interface circuit is required to work for both DC drive, and AC drive, good DC stability is required. Since the interface circuit is scaled to look like a transducer, its output is 25 uV/mmHg with a 5 VDC drive. If the drift error must be less than 1 mmHg over the operational temperature range of 10° C. to 40° C., the drift must be less than 0.833 uV/° C. Furthermore, DPT's are only allowed a DC offset of 1.875 mV (75 mmHg) by specification, so the interface circuit must meet that requirement as well.

Figure 8:
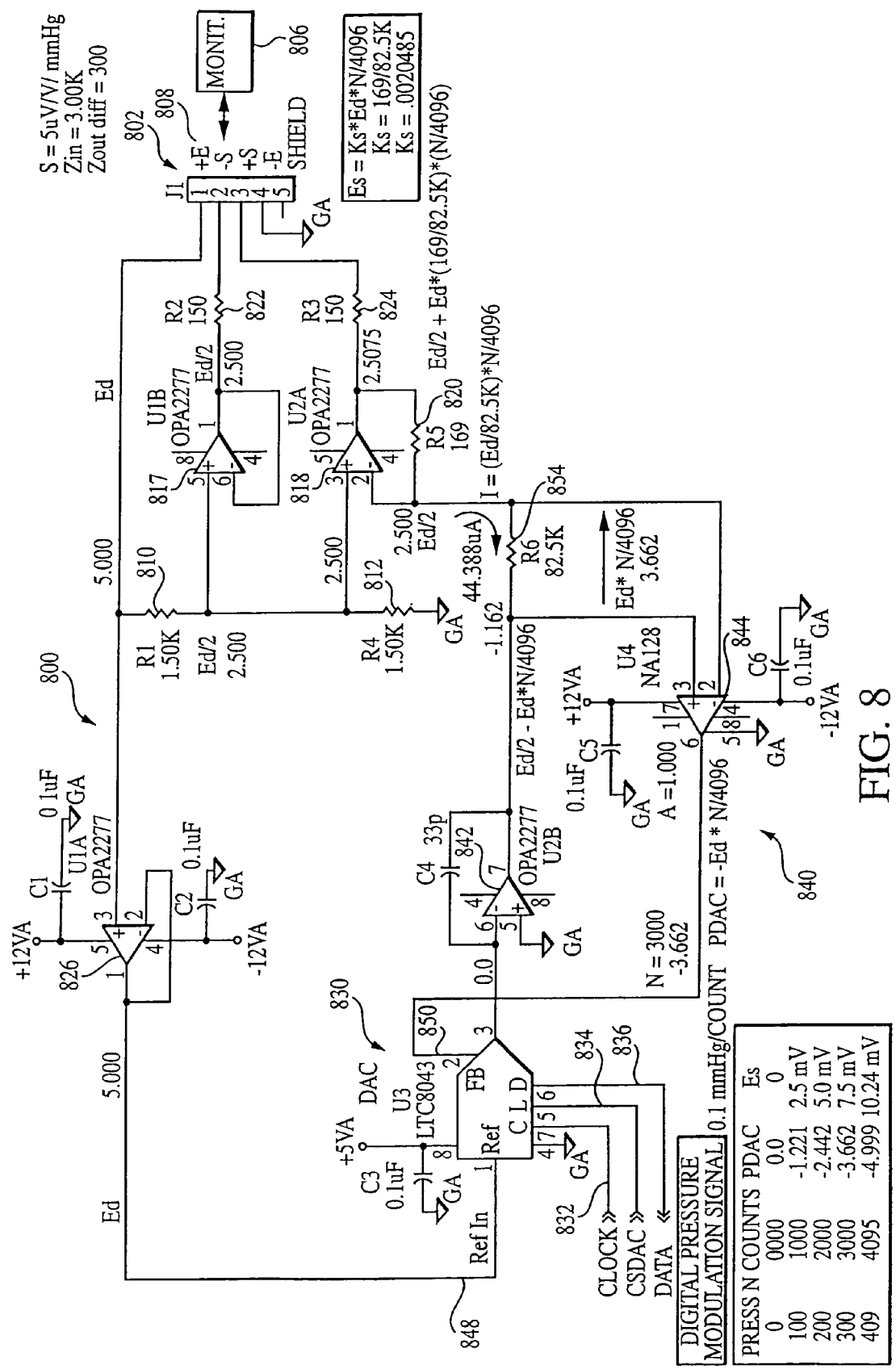
FIG. 8 is a schematic diagram of one exemplary embodiment of the interface circuit of the invention.

Referring now to FIG. 8, a first embodiment of the improved interface circuit 800 of the invention meeting the foregoing requirements is described. A shown in FIG. 8, the circuit 800 generally acts as an interface between the non-invasive blood pressure measurement system (such as that manufactured by the Assignee hereof) and prior art monitoring devices manufactured by any number of different entities which are adapted for passive bridge transducer or similar sensing devices (not shown). Specifically, jack or connector J1 802 connects to the monitor 806 which supplies drive excitation voltage $E_d$ at pin 1 (+E) 808. Resistors R1 810 and R4 812 provide the input impedance, nominally selected in the present embodiment to be 3K ohms. During operation with the aforementioned passive bridge device, the monitor 806 looks for such an impedance in order to determine if the passive bridge transducer is electrically connected. Alternatively, the monitor may detect the presence of a passive bridge transducer by looking for the signal at +S 814 or −S 816.

In the embodiment of FIG. 8, resistors R1 and R4 form a 2:1 divider and apply a signal of $E_d/2$ to the inputs of two operational amplifiers U1B 817 and U2A 818. The operational amplifiers 817, 818 each comprise Model No. OPA2277 integrated circuit (IC) amplifiers manufactured by Texas Instruments Corporation, although other types, integrated or otherwise, may be used. The construction and operation of such operational amplifiers are well known in the electronic arts, and accordingly are not described further herein. Both operational amplifiers are configured as voltage followers (assume no current flow in resistor R5 820 for purposes of the instant discussion), so that the voltage of their output signals are also represented by the relationship $E_d/2$. Resistors R2 822 and R3 824 couple the output signals of the amplifiers to the +S 814 and −S 816 terminals of the transducer output connector J1 802, and provide a differential output impedance of 300 ohms to the monitor, although it will be appreciated that other resistance values may be substituted. The aforementioned OPA2277 amplifier is an extremely low offset (e.g., 25 uV) and low drift (e.g., 0.1 uV/° C.) device, so the output offset is only on the order of 50 uV worst case (which corresponds to approximately 2 mmHg pressure). Total drift of this stage is only on the order of 3 uV over a 10° C. to 40° C. temperature range.

As shown in the exemplary embodiment of FIG. 8, the excitation voltage $E_d$ is buffered by unity gain amplifier U1A 826 of the type well known in the art, and applied to the reference input of a 12-bit, bipolar, multiplying digital-to-analog converter (DAC) U3 830. While the present embodiment uses a 12-bit DAC, it will be recognized that DACs having other bit resolutions (such as 8-bit, 10-bit, 14-bit, or 16-bit) and operating characteristics (e.g., "flash" DACs) may also be utilized. Note also that in the present embodiment, the DAC supports the bipolar multiplication function. The digital inputs 832, 834, 836 of the DAC 830 carry the blood pressure waveform signal of the present embodiment. Among other functions, the DAC 830 performs the required multiplication function described by the bridge transfer function, namely that of Eqn. 13

$$Ed \times P \qquad \text{(Eqn. 13)}$$

The DAC 830 is connected in a feedback loop 840 with operational amplifiers U2B 842 and U4 844 to form a bipolar, programmable, floating current source. In operation, the voltage at the reference input 848 of the DAC 830 causes an internal current to flow, the magnitude of which that is a function of the DAC count, N. This current flows through an internal feedback resistor (10K ohms in the present embodiment) connected to pin "2" 850 of the DAC 830. The DAC summing junction (not shown) is held at 0 volts by the feedback action of amplifier U2B 842. The output voltage at pin "2" of the DAC 830 is given by Equation 14:

$$PDAC = -Ed \times \frac{N}{4096} \qquad \text{(Eqn. 14)}$$

This signal is supplied by instrumentation amplifier U4 844, which is configured for a gain of 1 (unity) in the present embodiment. By virtue of its connection, the voltage across resistor R6 854 becomes:

$$ER6 = Ed \times \frac{N}{4096} \qquad \text{(Eqn. 15)}$$

Amplifier U2B 842 will adjust its output voltage to satisfy Eqn. 15 above. The voltage at the other end of resistor R6 854 is equal to $E_d/2$. Thus, the voltage at the output of amplifier U2B 842 becomes:

$$E(U2B7) = \frac{Ed}{2} - \left[Ed \times \frac{N}{4096}\right] \qquad \text{(Eqn. 16)}$$

The output current which flows through R6 854, also flows through R5 820, which adds to the signal at the output of U2A 818. It can be shown through analysis that the current flowing through R6 854 is given by the following relationship:

$$I = \frac{Ed}{R6} \times \frac{N}{4096} \qquad \text{(Eqn. 17)}$$

Where N is the count programmed into the DAC 830 via the serial-to-parallel interface (SPI) (pins "5", "6", and "7") 832, 834, 836. In the illustrated embodiment, N can be set for any value from 0 to 4095. Hence, if $E_d$ is 5.0 V and N=3000 counts, the current I will be 44.388 uA per Eqn. 17. Note that as the drive voltage $E_d$ reverses polarity, then the current I reverses direction, and the output signal at +S 814 reverses phase.

The current I develops a voltage across R5 820 given by the following equation:

$$ER5 = R5 \times \frac{Ed}{R6} \times \frac{N}{4096} \quad \text{(Eqn. 18)}$$

This makes the output at U2A 818 equal to:

$$E(+S) = \frac{Ed}{2} + \left[R5 \times \frac{Ed}{R6} \times \frac{N}{4096}\right] \quad \text{(Eqn. 19)}$$

Since the voltage at −S 816 is also $E_d/2$, then the differential output is:

$$Es = \frac{Ks \times Ed \times N}{4096} \quad \text{(Eqn. 20)}$$

where:

$$Ks = \frac{R5}{R6}, \text{ and } 0 \leq N \leq 4095.$$

Note that if the pressure P is substituted for the quantity N/4096, Eqn. 20 has the same form as the transfer function for the passive bridge previously described herein.

The ratio of R5 820 to R6 854 sets the sensitivity value for the circuit, and the scaling for the pressure transfer function. For example, for 5 uV/V/mmHg, Ks=0.002048. Note also that in the present embodiment, the constants are arranged so that the value of N scales as 0.1 mmHg/count. Thus N=3000 yields 3000×0.1=300 mmHg.

Additionally, in the present implementation, resistors R1 810 and R4 812 are selected to be low tempco (25 ppm/° C.) and matched to 0.1%. Resistors R5 820 and R6 854 are also low tempco types (10 ppm/° C.), and have accuracy better than or equal to 0.05%. Ideally, the resistors (R5 AND R6) should be a custom network in a common thermal environment so that differential thermal gradients are minimized. For the values of R5 820 and R6 854 shown, the nominal accuracy of the output signal is advantageously within 0.02% at 300 mmHg.

One of the advantages of the circuit 800 of the embodiment of FIG. 8 is that the circuit is capable of utilizing a digital representation of the blood pressure (BP) input signal, as opposed to requiring an analog representation of the BP signal. This capability is significant from the perspective that any deleterious effects on accuracy, drift, and non-linearity associated with the analog synthesis are avoided, since no conversion between the digital and analog domains is performed prior to input.

The circuit 800 is also advantageously ratio-metric with respect to the drive signal $E_d$ supplied by the monitor to which the circuit is connected. Specifically, any change in Ed is also reflected in the proper ratio at the outputs +S and −S. Also, the output scaling of the circuit 800 is adjustable, and the transfer function is inherently linear as described by equation 20, where Ks is the ratio of R5 to R6. As yet another advantage, digital processing of the (digital) BP signal is readily accomplished prior to inputting the signal to the DAC 830, so any BP signal anomalies and/or artifacts can be conveniently eliminated through signal processing techniques of the type well known in the art.

Since blood pressure is a dynamic (i.e., time variant) signal, it is necessary to send out a new digital representation of the BP value to the DAC 830 whenever the BP value changes. The Assignee hereof has noted that in an exemplary application, 1000 values per cardiac cycle provide sufficient resolution, although other values (higher or lower) may be used consistent with the invention. In such application, each value of N takes approximately 3 usec to load, so updating of the DAC 830 can be performed completely within 3 msec (i.e., 1000 values×3E-06 sec/value). In comparison, the fastest cardiac cycle occurs in roughly 250 msec. In practice, it can be shown that as few as 40 points per cardiac cycle is sufficient to define typical blood pressure waveform signatures. This allows a sample rate as low as 160 Hz for the DAC in order to accommodate cardiac cycles up to 240 beats per minute.

For the purposes of calibration, the DAC 830 can be set to N=0, and the attached monitoring device can be zeroed (via, for example, its front-panel transducer zero control). In the context of the previous example, the DAC 830 can then be set to N=1000, which correlates to 100 mmHg. This approach provides a constant output which is easily displayed on the monitor, and further provides a span calibration check. If for any reason the monitor displays a reading offset from the 100 mmHg calibration value, then that value can be readily compensated for, such as for example through insertion of an error term via the non-invasive blood pressure monitor (NIBPM) with which the circuit is associated. In one exemplary embodiment, the error term is entered through a keypad input device associated with the NIBPM device manufactured by the Assignee hereof, although other methods (software or otherwise) may be used with equal success.

Figure 9:
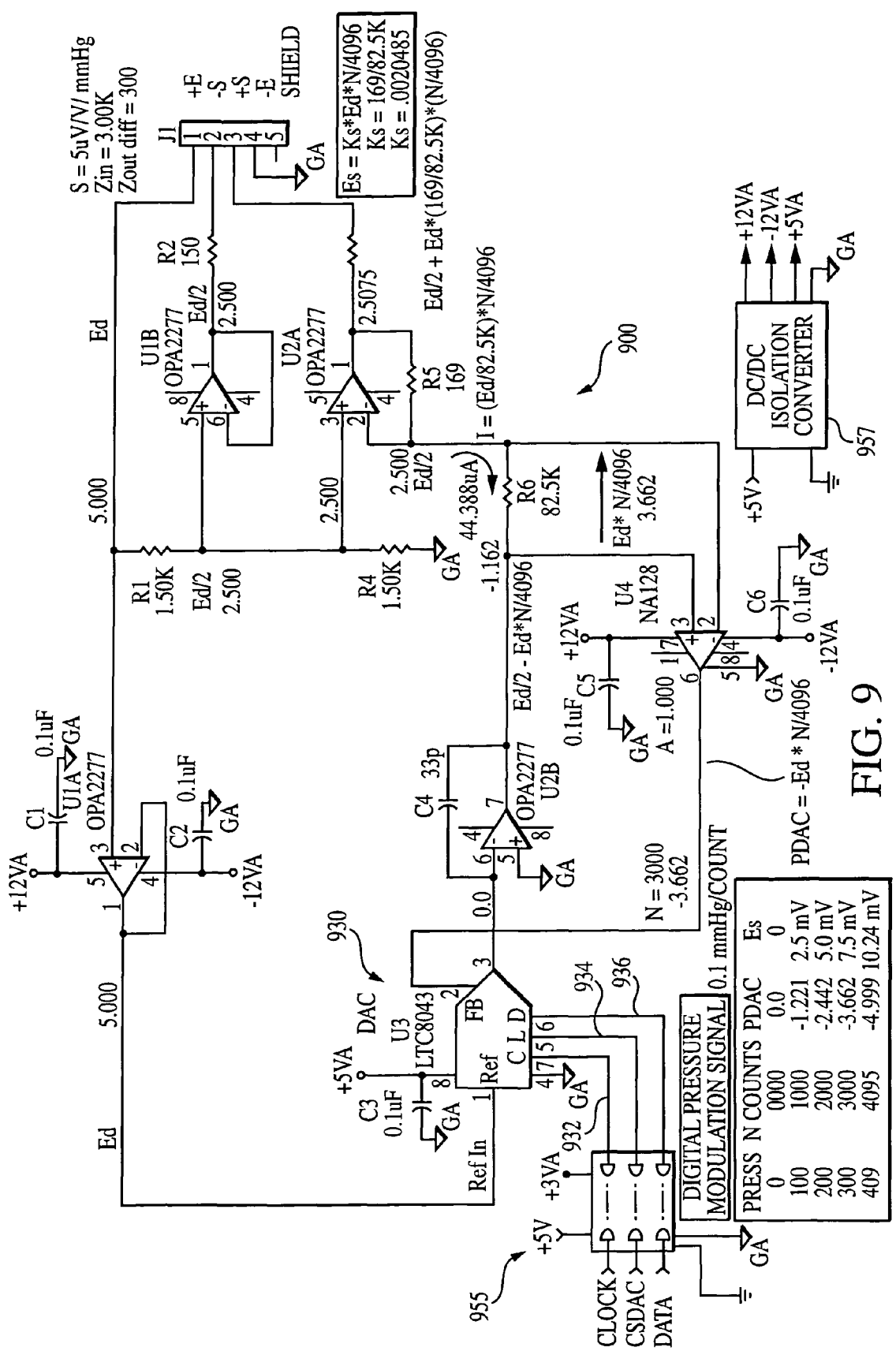
FIG. 9 is partial schematic of a second embodiment of the interface circuit of the invention, wherein optical isolators are disposed in the data path to the DAC, thereby providing electrical isolation.

In another embodiment of the interface circuit 900 of the invention (FIG. 9), the digital programming lines 932, 934, 936 to the DAC 930 are optically isolated via an optical isolator module 955, and an isolated power supply 957 of the type well known in the electronic arts used to power the circuit 900. This approach advantageously provides complete floating isolation of the interface circuit, and eliminates any potential for ground loops, compromise of patient and/or operator safety, and the like.

It will be recognized that while the foregoing embodiments of the interface circuit of the invention (i.e., FIGS. 8 and 9) are cast in terms of discrete electrical components (i.e., operational amplifiers, resistors, capacitors, etc.) arranged on an exemplary printed circuit board, the circuit, and even ancillary components associated therewith, may be embodied in one or more integrated circuit (IC) devices using any of the well understood semiconductor design synthesis and fabrication techniques known to those of ordinary skill. Such integrated circuit may even include the electronic components of the sensing device (e.g., NIBPM) if desired. For example, the signal processor, ADC, and interface circuit 800 may all be embodied as an application specific integrated circuit (ASIC) on a single silicon die. Other arrangements (including the use of multiple integrated circuit devices) are also contemplated, all such variants and alternate embodiments falling within the scope of the claims appended hereto.

Disconnect Circuit

Referring now to FIG. 10, one exemplary embodiment of the monitor disconnect circuit 1000 of the invention is described. This circuit 1000 detects the presence of an electrically connected patient monitoring device by detecting the drive signal the monitor uses to excite the normally connected passive bridge. Rather than detecting this signal directly, the circuit 1000 looks at a buffered version of the signal (Pin 1 of U1A 826 in FIG. 8), labeled $E_{dbuf}$ 1010 in FIG. 10.

The construction and operation of the disconnect circuit 1000 is now described. As illustrated in FIG. 10, the drive signal Ed is applied to comparators U8A 1012 and U8B 1014. The comparator threshold values are set by resistors R21 1016, R25 1018, and R27 1020 to a predetermined value, +/−1V in the illustrated embodiment. The wired "or" connection 1022 at the output of U8A 1012 and U8B 1014 forms a window comparator arrangement 1024 and transfer function, as illustrated in FIG. 10a. Thus, as long as some part of the drive signal waveform exceeds the magnitude of the predetermined value (e.g., |1V|), the output of the window comparator 1024 will be low. This configuration ensures that any signal, whether DC or AC, and of any shape or duty cycle, will be detected by the window comparator formed by the comparators 1012, 1014 and output connection 1022. The low output impedance of the window comparator arrangement discharges capacitor C11 1026 through resistor R24 1028. As long as the voltage across C11 1026 is less than the threshold of comparator U9A 1030 (e.g., +1V), the output of comparator U9A 1030 will be low. If the drive signal $E_d$ is lost due to an electrically disconnected monitor, then the output of the window comparator arrangement 1024 goes to a high impedance state, and C11 1026 starts to charge to a selected voltage (e.g., +5V) through resistor R22 1034. When the voltage across C11 1026 exceeds the predetermined value (e.g., +1V), comparator U9 1030 output goes high indicating that the monitor is electrically disconnected. The time constant ($\tau$) for this detection is set by R22 1034 and C11 1026, and is approximately 100 mS for the values shown in the illustrated embodiment. The use of a comparatively long time constant in the illustrated embodiment ensures that momentary loss of signal, such as periodic zero-crossings of a sine wave drive signal, are not detected by the circuit 1000. For the aforementioned 100 mS time constant, the drive signal frequency can advantageously drop as low as about 100 Hz. In actual practice however, the drive signal frequency received by the circuit will characteristically remain much higher, typically on the order of 2 to 5 KHz.

It is noted that the output from comparator U9A 1030 comprises a logic level-compatible signal that can be read by an input/output (I/O) port of any processor running from a 5V 1042 supply. Note that since U9A 1030 is an open collector comparator, R23 1038 can be returned to any supply voltage such as 1.5V, 1.8V, or 3.3V for compatibility with a wide range of modern microprocessors or other parts.

Alternate Embodiment of Interface (and Disconnect) Circuit with Self-Test

Referring now to FIG. 11, yet another embodiment of the interface circuit (with disconnect circuit) of the present invention is described. It will be noted that in the embodiment of FIG. 11, the circuit 1100 is adapted to provide enhanced functionality in various aspects as compared to the embodiment of FIGS. 8 and 10, and FIG. 9, including self-test functionality, as described in greater detail below. The circuit 1100 of FIG. 11 also has greater complexity, however, and accordingly may be optimal for applications where its enhanced functionality is required and/or where the increased cost is not a significant issue.

As shown in FIG. 11, the supply voltages for the various analog circuitry of the interface circuit 1100 are set to +/−7.5 in order to reduce the power requirements and heat generation rate of the circuit 1100, and to increase its reliability. Additionally, the amplifier U11B 1126 buffers the drive voltage Ed 1108 (+E) after the voltage divider formed by R19 1110 and R17 1112, as compared to the arrangement of FIGS. 8 and 10. The output of U11B 1126 is also configured to drive the reference input 1148 of the DAC U6 1130, and the comparators U1A 1170, and U1B 1172, via switch S1B 1174. The voltage Ed/2 1162 is also made available to the A/D converter (not shown) for measurement. Furthermore, in order to compensate for the scale factor error that occurs due to this configuration, the resistance values of resistors R7 1120, and R8 1154 have been changed, with the ratio of 244.1:1. These modifications keep the circuit scale factor at 10 counts/mmHg.

Additionally, the reference voltages for the window comparator U1A 1170, and U1B 1172 of the circuit 1100 have been changed from +/−1 V to +/−0.5V. This is accomplished by changing the values of the resistors in the divider; R3 1176, R4 1178, and R5 1180.

As shown in FIG. 11, the output comparator for the monitor detector circuit utilizes a Schmidt trigger logic gate, NC7WZ14 1181. Its output can drive either 3.3V or 5 V logic devices, although it will be recognized that other devices adapted to provide similar functionality yet different dive voltages, may be substituted. The output of the comparator 1181 is read directly by the microprocessor (or other comparable processing device).

The circuit 1100 of FIG. 11 also includes radio frequency interference (RFI) protection via choke T1 1165, and capacitors C17 1166, C22 1167, C24 1168, and C28 1169. Electrostatic discharge (ESD) protection of the patient monitor connector output 1102 is also provided via over-voltage clamp U9 1184. As a result of this protection, the range of the patient monitor drive voltage (+E) 1108 is limited to +/−7.5V, or 15 V p-p.

As previously referenced, the circuit 1100 of FIG. 11 also includes a self-test sub-circuit 1177, which provides an independent means of insuring that the output signal to the patient monitor 806 is correct. This circuitry 1177 is now described in greater detail.

In order to have an independent means of insuring that the patient monitor circuit is functioning correctly, the unknown external drive voltage from the patient monitor (PM) 806 is disconnected, and a known reference signal 1185 used instead. In the illustrated embodiment, the known reference is generated by a precise voltage reference device (not shown), which provides +2.500 volts to S1A 1186. S1A 1186 and S1B 1174 effectively form an electronic single pole double throw switch which is controlled by the state of control line TMAI 1187. In normal operation S1A is off, and S1B is on. When it is desired to check the function of the PM circuit, TMAI 1187 is asserted true, and S1A 1186 turns on and S1B 1174 turns off. This disconnects the external PM drive signal and connects the known +2.5 V reference to the DAC U6, 1148 U7A 1117, U7B 1118, U1A 1170, and U1B 1172. The MONITOR output 1182 should go high for this condition, and can be verified by the microprocessor. This checks the ability of the circuit to detect connection to the PM. To the circuit, the +2.5 V reference behaves the same as a +5.000 V drive signal from the external PM. The 2.5V reference 1185 can be read by a second A/D converter (not shown) via the output of buffer U11A 1188 at REFMON 1189. This advantageously provides an independent check of the reference.

To verify the zero offset condition of the circuit 1100, the DAC 1130 is now set to a count of 0000. Under this condition, which simulates a 0 mmHg signal, the outputs of U7A 1117, and U7B 1118 are nominally +2.500 volts. Ideally their difference would be zero, but both amplifiers have a finite offset of up to 25 uV in the illustrated embodiment. The differential output can therefore be as much as 50 uV, which is equivalent to 2 nm hg for a 5 V drive. In order to measure this output signal U10 1190 is connected across the outputs of U7A 1117 and U7B 1118 through resistors R13 1122 and R6 1124. U10's gain is set to 400 via R16 1191 and R15 1192. The output signal TLFDBK 1193 thus has a scale factor of 10 mV/mmHg. For the zero condition, TLFDBK 1193 will be in the range of +/−20 mV. The network of R14 1194, C23 1195, R12 1196, and C18 1197 at the input of U10 1190, form a single pole low pass filter with a nominal cutoff frequency of 1.6 KHz when configured as illustrated. This filter prevents high frequency signals from entering U10 1190, and affecting its output. U10 1190 itself has an offset which can be as much as 50 uV. This offset must also be compensated since it represents +/−2 mmHg as well. Switch S1C 1198 is used for this purpose. Switch S1C 1198 is placed across the outputs U7A 1117, and U7B 1118 through resistors R13 1122 and R6 1124. Switch S1C 1198 is turned on ZMAI 1199 is asserted true (logic 0). This shorts out the differential offset error of U7A 1117, and U7B 1118 and allows the A/D converter (not shown) to measure the offset error of U10 1190 at TLFDBK 1193. Switch S1C 1198 is then opened, and the A/D (not shown) again measures the output of U10 1190 at TLFDBK 1193. This value represents the true "zero" signal being presented to the PM, and can become the baseline against which all non-zero outputs are referenced.

It should be noted that by making differential measurements as in the present embodiment, all of the offset errors in the A/D measurement channel advantageously cancel out. If either measurement falls outside a predetermined range, then a fault condition exists, and an alarm is generated (e.g., visual, audible, etc.), or other condition enabled (such the writing of data to a trace file). Note that the external PM must be zeroed to compensate for the small differential output of +/−2 mmHg. This is done when TMAI 1187 is 0, ZMAI 1199=1, and DAC 1130 count=0000.

To verify the gain accuracy of the circuit 1100, the DAC 1130 is set to a count of 1000. This should result in an output signal to the PM representing a predetermined value (e.g., 100 mmHg). Since U10 1190 is scaled at 10 mV/mmHg, its output signal TLFDBK 1193 should be 1.000 V above the zero reference value established earlier. If the measurement falls outside a predetermined range, then a fault condition exists, and an alarm (or other condition) is generated. If both the zero offset and gain of the PM circuit are verified as OK, then the circuit is reset to its normal condition: TMAI 1187=0, and ZMAI 1199=1.

Another advantageous aspect of the self test sub-circuit 1177 is that it can assess the proper operation of the monitor adapter interface circuit 1100 during normal operation if the external PM uses a constant DC drive signal. This is true for most modern monitors, although some still use either a sine wave AC drive, or a pulsed DC drive. When a fixed DC drive is used, the A/D converter can measure the value of the drive signal at ED/2 1162. By knowing this, the output for any pressure signal value can be computed, and compared against the actual measured output at TLFDBK 1193. If these values don't agree within a predetermined range, a fault condition exists, and appropriate alarms would be generated (or other action taken). As an example of the foregoing, assume the external patient monitor drive is +6.000 Volts. The A/D would measure +3.000 volts at ED/2 1162. Knowing that the actual drive voltage is 2×+3.000=+6.000 volts, the output signal can be computed as in Eqn. 21 below:

$$E_s = (5\ \text{uV/V/mmHg}) \times (+6.000\text{V}) \times 400 \times P_{out}, \quad \text{(Eqn. 21)}$$

where $P_{out}$ is expressed in mmHg. For a $P_{out}$ value of 100 mmHg, (DAC 1130 count=1000) $E_s$ will be equal to +1.200 V. $E_s$ would be measured at TLFDBK 1193. Note that in the illustrated embodiment, the output signal must be referenced to a zero value DAC 1130=0000, in order to cancel out the offset errors.

If the external PM 806 uses either a sine wave AC drive, or a pulsed DC drive, then operation can only be verified by switching to the +2.500 V reference. This can be done when the system first powers up, or when monitoring is suspended for some reason.

Method of Simulating Time Variant Output

Figure 12:
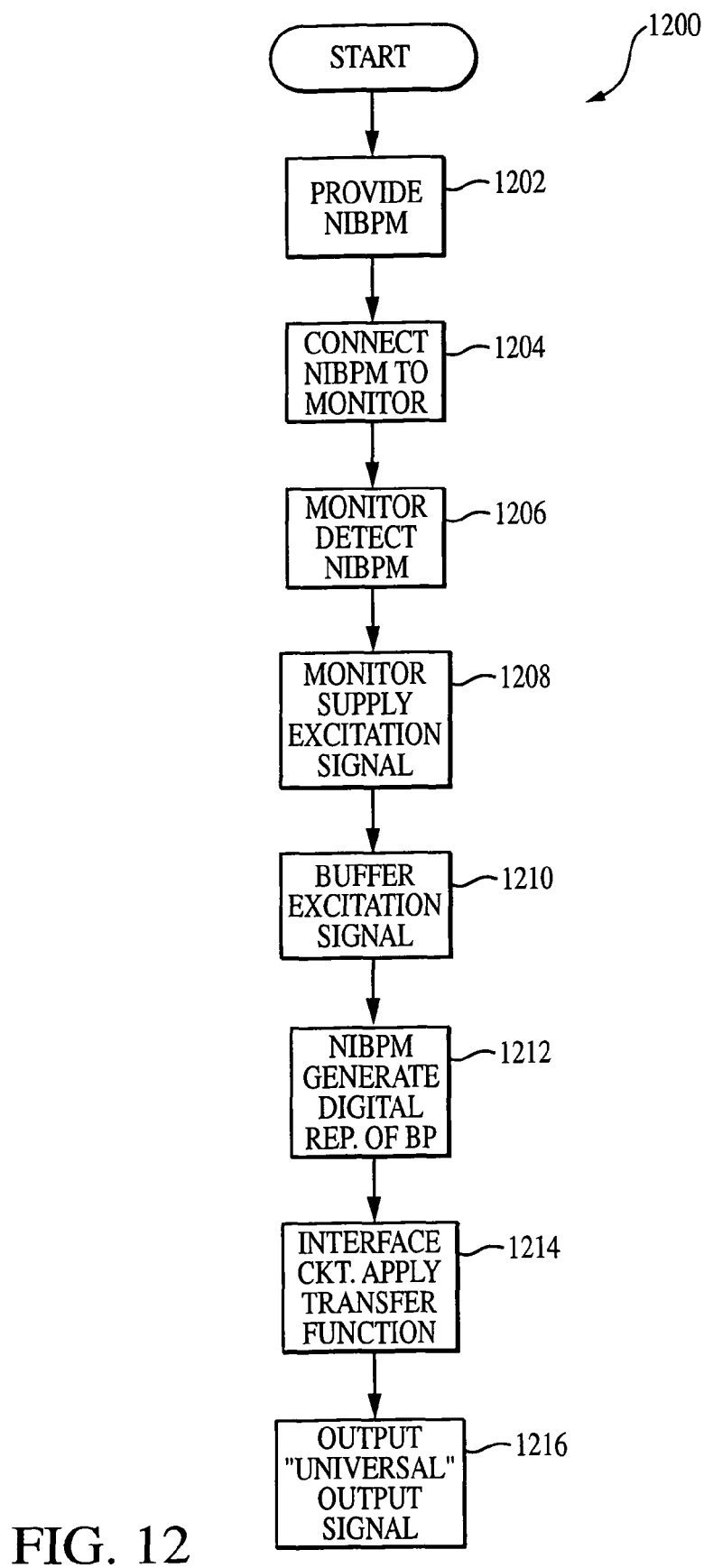
FIG. 12 is a logical flow diagram illustrating one exemplary embodiment of the method of simulating the time-variant output of a first device using a second device adapted according to the present invention.

Referring now to FIG. 12, the method for simulating a time-variant output signal from a first device using a second device according to the invention is described. It will be recognized that while the following discussion is cast in terms of a passive bridge transducer device such as those previously described ("first device") and its associated monitor, and a non-invasive blood pressure monitor ("second device"), the methodology of the invention may be readily applied to other applications and combinations of devices both within and outside the medical field, such as for example pressure measuring devices in industrial fluidic systems.

As shown in FIG. 12, the first step 1202 of the method 1200 comprises providing the non-invasive blood pressure monitor (NIBPM); a tonometric pressure-based system such as that manufactured by the Assignee hereof is used in one embodiment, although myriad other types and configurations may be substituted. The NIBPM is then electrically connected to one of the aforementioned prior art patient monitoring systems (e.g., those manufactured by General Electric, et al), per step 1204. The connection of the NIBPM is optionally detected in step 1208 through the presence of a specified impedance across two or more terminals in the patient monitor (or alternatively, a voltage at a predetermined terminal of the patient monitor), based on an applied excitation voltage provided to the NIBPM by the patient monitor (step 1206). In step 1210, the excitation signal is buffered within the interface circuit 800, 900, 1100 as previously described. Note that any of the foregoing interface circuits 800, 900, 1100 (or combinations of the desirable features thereof) may be used consistent with the method 1200.

In step 1212, the NIBPM generates a digital representation of the time-variant blood pressure waveform(s) through the data generated by pressure transducer elements (and optionally, acoustic transducer elements if so equipped) associated therewith. Generation of this signal is completely independent of the excitation signal applied by the monitor. The transfer function is next applied to the digital representation (step 1214) using the interface circuit 800, 900, 1100, the transfer function being substantially similar to that for the passive bridge device as previously discussed.

Lastly, the output signal from the interface circuit 800, 900, 1100 is produced which is compatible with the patient monitoring system (as well as being "universally" compatible with the patient monitoring systems of other vendors) per step 1216. The output signal of step 1216 is based at least in part on the digital representation of the waveform (e.g., blood pressure) provided to the DAC 830, 1130 of the circuit 800, 900, 1100, respectively, the applied drive signal 802, 1102 from the patient monitor 806, and the applied transfer function, the output signal being substantially similar to that produced by the passive bridge device under comparable excitation signal and measured pressure waveform.

Apparatus for Hemodynamic Assessment

Figure 13:
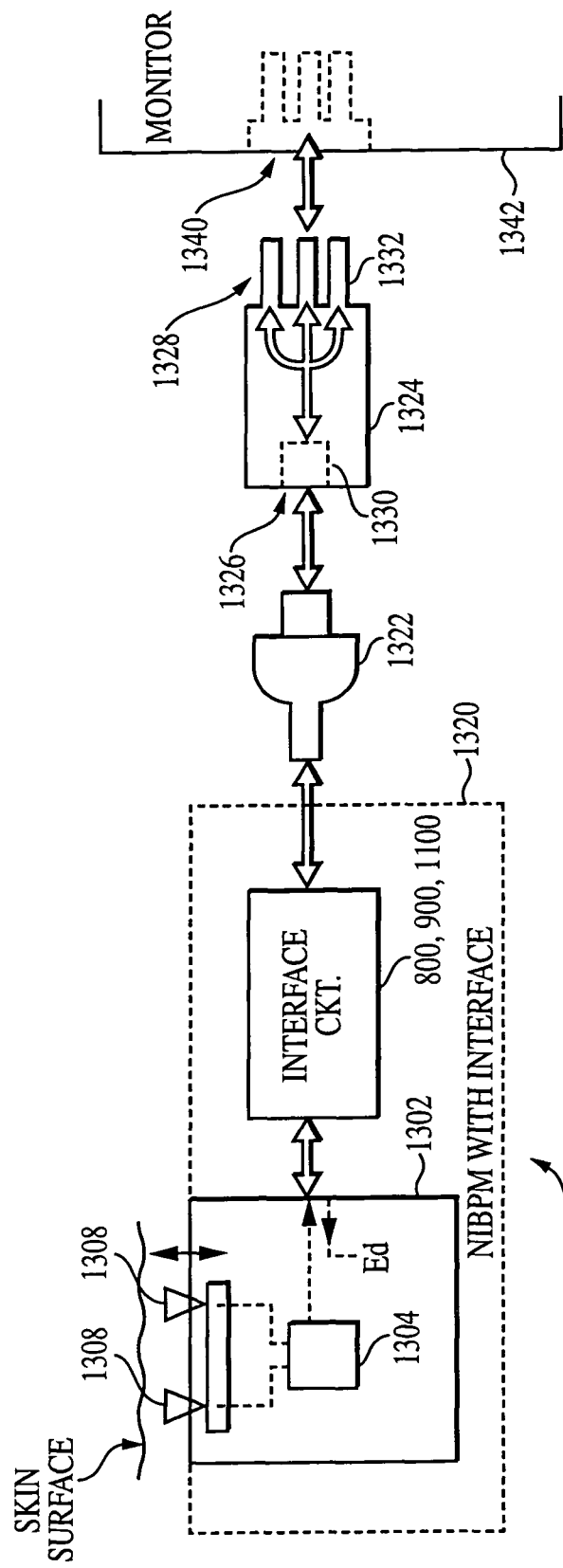
FIG. 13 is a functional block diagram of one exemplary embodiment of the apparatus for non-invasively measuring the blood pressure of a living subject according to the invention.

Referring now to FIG. 13, an improved apparatus for non-invasively assessing hemodynamic parameters (e.g., arterial blood pressure) associated with a living subject is described. In the exemplary embodiment of FIG. 13, the apparatus 1300 comprises, inter alia, (i) a blood pressure measurement system 1302 adapted to measure the blood pressure and/or other hemodynamic properties (such as for example blood kinetic energy or velocity) associated with the subject, and develop at least one binary digital signal related thereto; and (ii) the interface circuit 800, 900, 1100 previously described. The blood pressure/hemodynamic parameter measurement system 1302 comprises generally a signal processor 1304 operatively coupled to one or more pressure transducers 1308, as well as an applanation device 1310 adapted to control applanation pressure applied to the transducer(s) 1308. The signal processor 1304 (and associated algorithms running thereon) determine arterial blood pressure based on the measured data. One key advantage of the present invention, in addition to its effectively universal adaptability to various types of monitors as previously described, is its adaptability to any number of different parametric measurement devices, whether adapted for medical applications such as blood pressure measurement or otherwise. For example, the present invention may be readily used with the apparatus and techniques described in detail in co-pending U.S. patent application Ser. No. 09/534,900, entitled "Method And Apparatus For Assessing Hemodynamic Parameters Within The Circulatory System of A Living Subject" filed Mar. 23, 2000, assigned to the Assignee hereof, and incorporated herein by reference in its entirety, may be utilized. As yet another alternative, the methods and apparatus of co-pending U.S. patent application Ser. No. 09/815,080 filed Mar. 22, 2001 and entitled "Method And Apparatus For Assessing Hemodynamic Parameters Within The Circulatory System Of A Living Subject", also assigned to the Assignee hereof and incorporated herein by reference in its entirety, may be used with the present invention. It will be recognized, however, that yet even other techniques for measuring blood pressure may be employed by the blood pressure/hemodynamic assessment apparatus 1300 of the invention, including for example the time-frequency distribution based system disclosed in co-pending U.S. patent application Ser. No. 09/342,549, entitled "Method and Apparatus for the Noninvasive Determination of Arterial Blood Pressure" filed Jun. 29, 1999, or co-pending U.S. patent application Ser. No. 09/489,160, entitled "Method and Apparatus for the Noninvasive Determination of Arterial Blood Pressure" filed Jan. 21, 2000, both assigned to the Assignee hereof, and both incorporated herein by reference in their entirety. More broadly, literally any type of sensing apparatus which produces an electrical output (whether for measuring physiologic parameters or otherwise) may be utilized consistent with the invention.

The digital domain blood pressure data generated by the exemplary measurement system 1302 is fed to the interface circuit 800, which conditions the signal as previously described so as to allow seamless data communication with the selected patient monitor. As previously discussed, the interface circuit 800 is adapted to communicate data with literally any type of patient monitor device (regardless of manufacturer), and hence the apparatus 1300 of FIG. 13 may advantageously be used to non-invasively measure blood pressure from a subject irrespective of the in situ patient monitoring equipment available.

The apparatus of FIG. 13 is further adapted to be physically contained within a unitary or discrete device 1320 with associated electrical connector 1322 such that the connector 1322 may be plugged directly into the corresponding electrical receptacle within the in situ patient monitoring device. Since the receptacle configuration generally varies from monitor to monitor, the connector 1322 may be configured to mate with an adapter 1324 which receives the connector 1322 of the device 1320 in a first portion 1326, and mates with the associated receptacle 1340 of the patient monitoring device 1342 via a second portion 1328. In the illustrated embodiment, the adapter 1324 comprises a female-male plug (i.e., the connector 1322 of the NIBPM device 1320 is received in a female connector 1330 in the first portion 1326, and the male connector 1332 disposed on the second portion 1328 is received in the corresponding patient monitor female receptacle 1340). Such patient monitor female receptacle configuration is widely used for purposes of reducing electrical shock hazard, since the electrical terminals carrying excitation voltage to the sensing apparatus 1300 are shielded from casual contact. It will be recognized, however, that other arrangements may be employed in the adapter 1324 consistent with the invention, including for example female/female, male/male, and male/female (as differentiated from female/male in the embodiment of FIG. 13). Furthermore, ganged or multiple adapter configurations may be employed, such as in the case where it is desirable to have (i) two or more NIBPM devices 1320 (or devices of mixed configuration) electrically communicating with a sole patient monitor 1342. Other configurations and variations on the foregoing themes are possible, all such configurations and variations falling within the scope of the claims appended hereto.

Furthermore, it will be readily apparent that the connector 1322 of the apparatus 1300 may be adapted to be received directly by or within the receptacle 1340 of the selected monitor 1342. For example, if certain medical/treatment facilities uniformly utilize only one type of patient monitor, they may wish to procure NIBPM devices with connectors 1322 which are adapted for direct receipt by the receptacle 1340 of that type of patient monitor, thereby obviating the need for separate adapters (and any cost, safety, or electrical performance issues potentially relating thereto.)

Figure 13A:
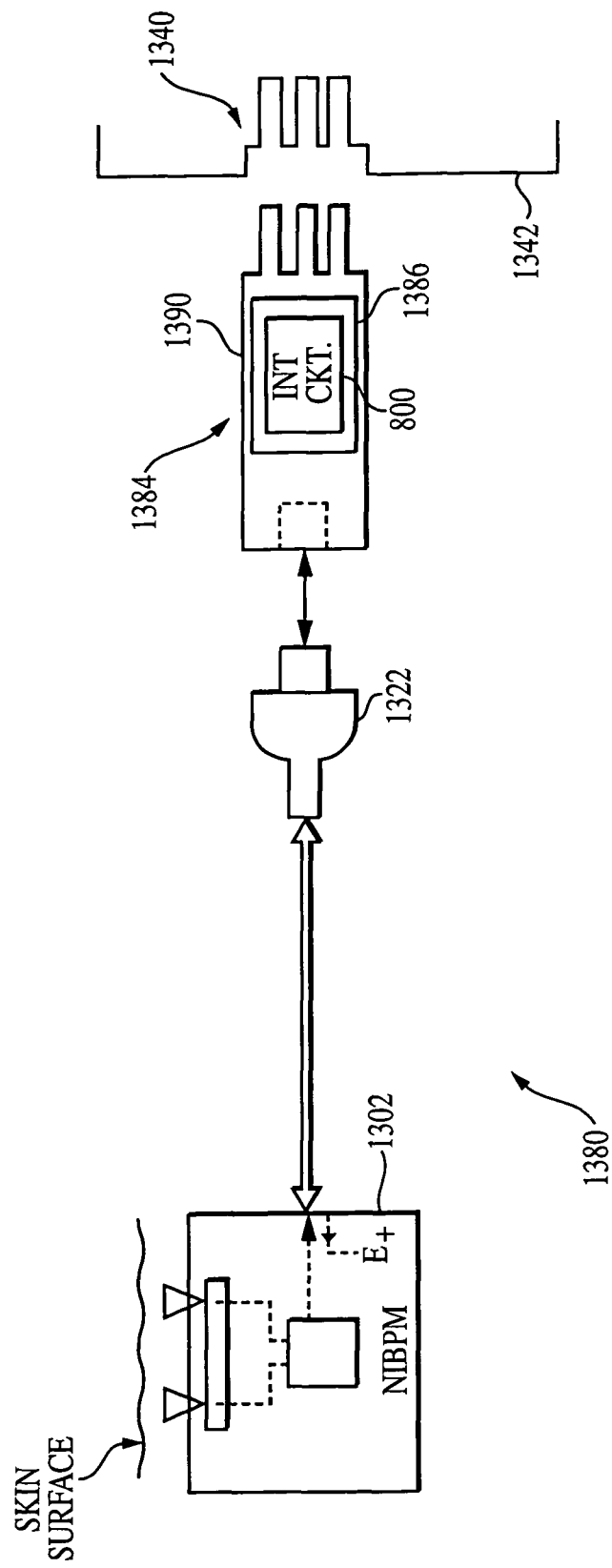
FIG. 13*a* is a functional block diagram of a second embodiment of the apparatus for non-invasively measuring the blood pressure of a living subject, wherein the interface circuitry is disposed proximate to the patient monitor.

Referring now to FIG. 13a, a second embodiment of the apparatus for noninvasively assessing hemodynamic parameters associated with a living subject is described. In the embodiment of FIG. 13a, the apparatus 1380 is configured such that the interface circuit 800, 900, 1100 is disposed proximate to the patient monitor 1342, specifically as part of the adapter 1384 used to couple the connector 1322 to the patient monitor receptacle 1340. The interface circuit components (including DAC, comparators, amplifiers, resistors, capacitors, etc.) are disposed on a small form factor substrate 1386 such as a printed circuit board. Miniature circuit boards are well known in the microelectronic/surface mount electronics arts, and accordingly are not described further herein. The interface circuit 800, 900, 1100 is then electrically disposed in the circuit path between the NIBPM digital data output and patient monitor receptacle 1340, such that (i) the digital data produced by the NIPBM is provided to the input terminals of, e.g., the DAC 830 (see FIG. 8), and the ground, excitation (Ed), and reference potentials necessary to operate the interface circuit are provided to the appropriate points in the circuit 800, 900, 1100. The substrate 1386 with components is physically contained in an over-molding 1390 which encapsulates the assembly in a polymer/elastomeric material, thereby increasing its durability and resistance to external effects such as temperature variation, moisture, dust, electromagnetic noise, and physical trauma. The assembly is also optionally electromagnetically shielded using, for example, a grounded tin-copper alloy metallic shield element of the type well known in the art, such shield being disposed within the over-molding 1390.

Figure 14:
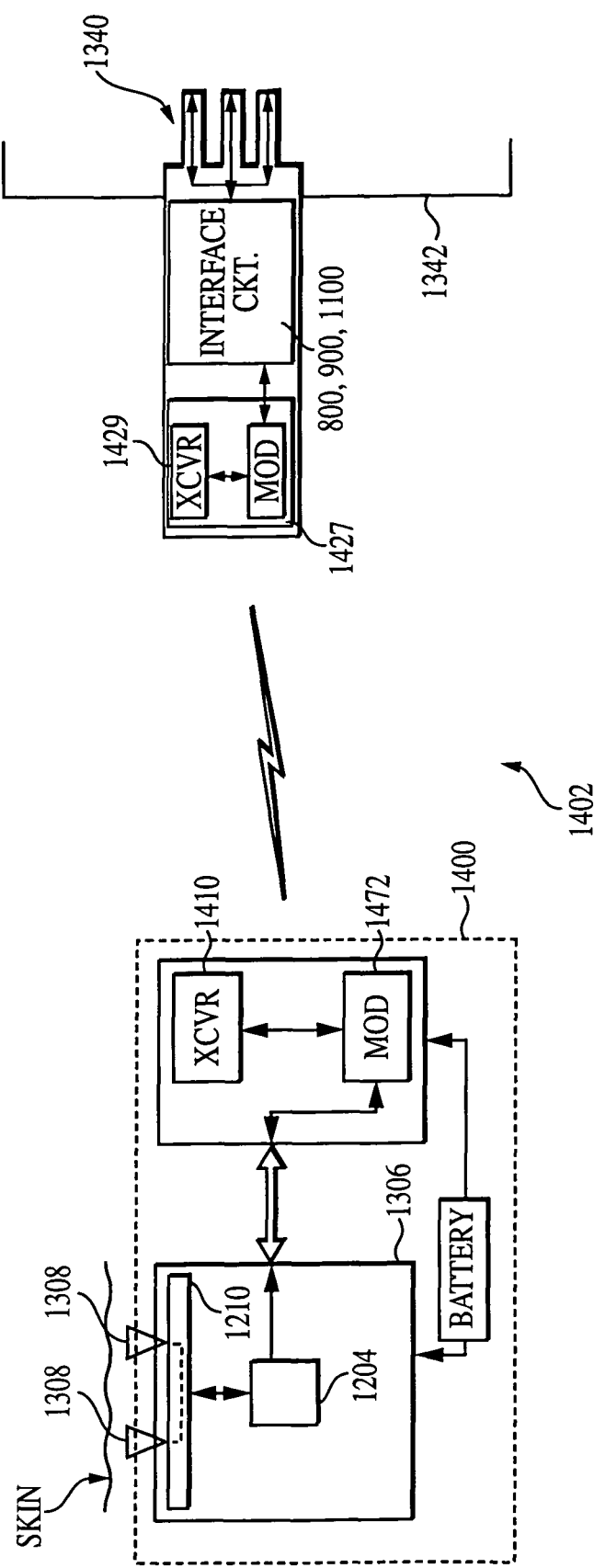
FIG. 14 is a functional block diagram of a third embodiment of the apparatus for non-invasively measuring the blood pressure of a living subject, incorporating a wireless (e.g., radio frequency ISM band) data link.

In yet another embodiment, shown as FIG. 14 herein, the apparatus of FIG. 13 (and patient monitor) may be configured to include a wireless link 1402 between the apparatus 1400 and the patient monitor 1342, such that the interface circuitry 800, 900, 1100 is disposed proximate to the patient monitor 1342. As illustrated in FIG. 14, the link 1402 comprises a radio frequency (RF) communications system of the type well known in the electrical arts. For example, in one exemplary variant, an RF transceiver 1410 and modulator device 1472 are provided and adapted to generally comply with the well known "Bluetooth™" wireless interface standard. The Bluetooth "3G" wireless technology allows users to make wireless and instant connections between various communication devices, such as mobile devices (e.g., cellular telephones, PDAs, notebook computers, local or remote patient monitoring stations, and the like) and desktop computers or other fixed devices. Since Bluetooth uses radio frequency transmission, transfer of data is in real-time. The Bluetooth topology supports both point-to-point and point-to-multipoint connections. Multiple 'slave' devices can be set to communicate with a 'master' device. In this fashion, the NIBPM device 1406 of the present invention, when outfitted with a Bluetooth wireless suite, may communicate directly with other Bluetooth compliant mobile or fixed devices including the patient monitor receiver 1427 disposed at the monitor 1342, or alternatively other Bluetooth-capable devices such as a cellular telephone, PDA, notebook computer, or desktop computer.

The monitor receiver 1427 comprises a Bluetooth compatible transceiver 1429 adapted to receive binary digital data in the form of radiated RF energy from the corresponding transceiver 1410 on the NIBPM device, and decode the binary data for input to the DAC 830 of the interface circuitry 800, 900, 1100. Hence, the operation of the wireless link 1402 is effectively transparent to the interface circuit and patient monitor 1342.

Figure 14A:
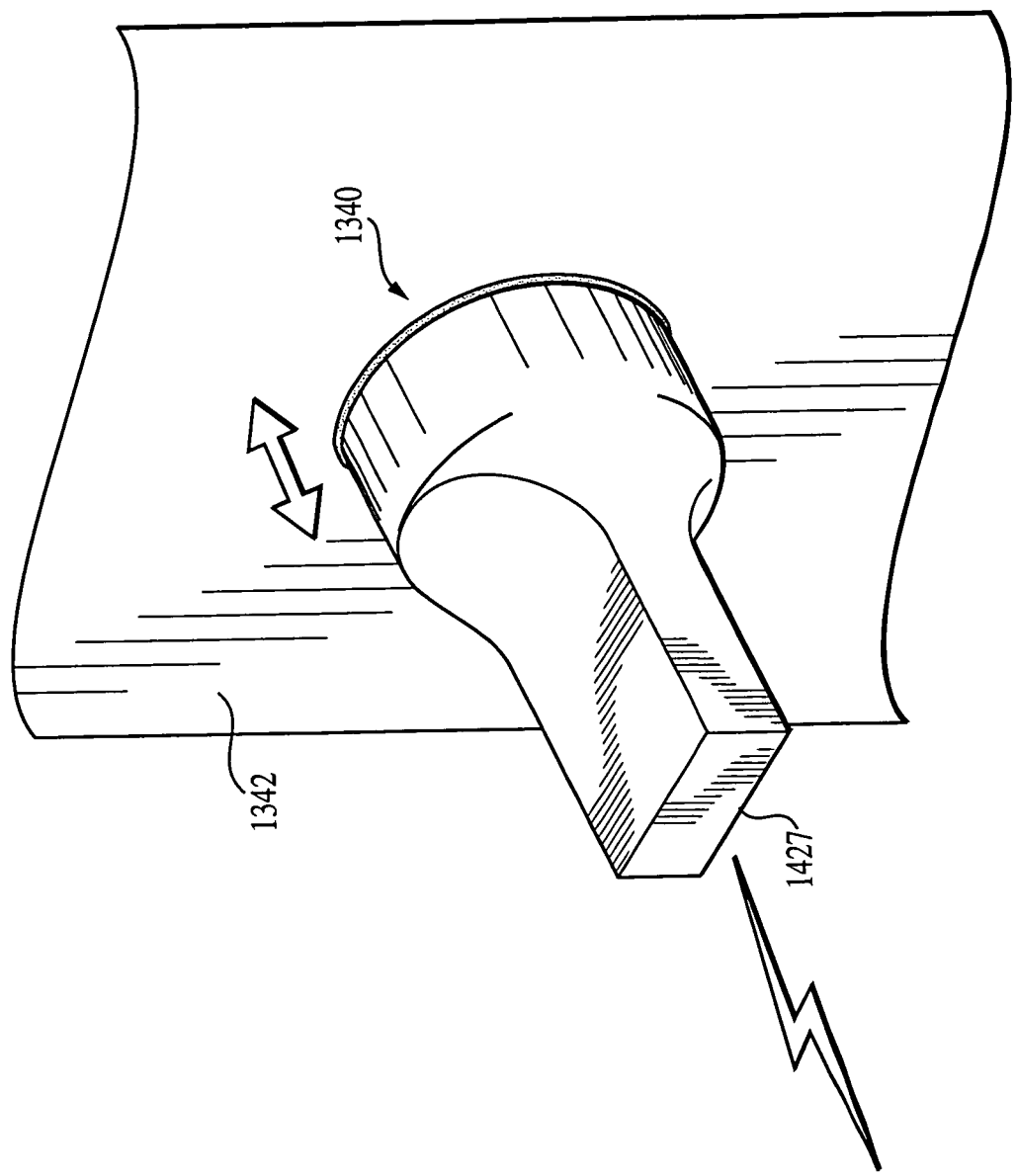
FIG. 14*a* is a perspective view of one embodiment of the monitor receiver unit of the apparatus of FIG. 14, illustrating the form factor thereof.

The monitor receiver unit 1427 is configured physically to mate with the patient monitor receptacle 1340 (either directly or via an interposed adapter 1324, as previously described), such that the unit 1427 may be simply "plugged in" to the receptacle 1440 and remain free-standing. The Bluetooth transceiver 1429 of the unit 1427 and components of the interface circuit 800, 900, 1100 (as well as other attendant electronic components) are readily contained within the rectangular form factor (FIG. 14a) of the receiver 1427, although it will be appreciated that other forms may be utilized (such as a cylinder, sphere, square, etc.). Additionally, it will be recognized that for purposes of saving space within the apparatus 1400, the signal processing and transceiver/modulator components of the NIBPM device 1400 may be embodied in a fully integrated "system on a chip" (SoC) application specific integrated circuit (ASIC) of the type generally known in the semiconductor fabrication arts (not shown). The SoC ASIC incorporates, inter alia, a digital signal processor (DSP) core, embedded program and data random access memories, RF transceiver circuitry, modulator, analog-to-digital converter (ADC), and analog interface circuitry necessary to support sampling, conversion, processing, and transmission of the blood pressure (or other) data to the receiver 1427. The SoC device design is generated using VHSIC Hardware Description language (VHDL) in conjunction with design and synthesis tools of the type well known in the art. A 0.18 micron MOS-based process is used to fabricate the device of the illustrated embodiment, although other semiconductor fabrications processes including for example 0.35 micron or 0.1 micron may be substituted, depending on the degree of integration required.

Alternatively, a number of different subjects undergoing blood pressure monitoring/analysis using the NIBPM of the present invention (or other comparable devices) may be monitored in real time at a centralized location using a single monitor receiver 1427. Specifically, the monitor receiver 1427 and transceiver 1429 are adapted to receive a plurality (currently seven, under prevailing Bluetooth architecture, although such number may be increased or decreased) of signals from remote devices (e.g., NIBPMs), whereby the individual signals may be multiplexed or alternatively processed in parallel by the interface circuit 800, 900, 1100 (with the addition of appropriate multiplexing or parallel processing hardware of the type well known in the electronic arts). Hence, a patient monitor 1342 configured to receive such multiplexed or parallel channel data may be used to monitor multiple subjects at once.

Bluetooth-compliant devices, inter alia, operate in the 2.4 GHz ISM band. The ISM band is dedicated to unlicensed users, including medical facilities, thereby advantageously allowing for unrestricted spectral access. Maximum radiated power levels from the transceiver 1410 of FIG. 14 are in the mW range, thereby having no deleterious effect on the physiology of the subject due to radiated electromagnetic energy. As is well known in the wireless telecommunications art, radiated power from the antenna assembly (not shown) of the transceiver 1410 may also be controlled and adjusted based on relative proximity of the transceiver 1410, thereby further reducing electromagnetic whole body dose to the subject.

The modulator 1412 of the illustrated embodiment uses one or more variants of frequency shift keying, such as Gaussian Frequency Shift Keying (GFSK) or Gaussian Minimum Shift keying (GMSK) of the type well known in the art to modulate data onto the carrier(s), although other types of modulation (such as phase modulation or amplitude modulation) may be used.

Spectral access of the device may be accomplished via frequency divided multiple access (FDMA), frequency hopping spread spectrum (FHSS), direct sequence spread spectrum (DSSS, including code division multiple access) using a pseudo-noise spreading code, or even time division multiple access, depending on the needs of the user. For example, devices complying with IEEE Std. 802.11 may be substituted in the probe for the Bluetooth transceiver/modulator arrangement previously described if desired. Literally any wireless interface capable of accommodating the bandwidth requirements of the system may be used. As yet another embodiment, an infrared device (e.g., Infrared Data Association "IrDA") may be substituted or even used in conjunction with the aforementioned RF link 1402.

Method of Providing Treatment

Figure 15:
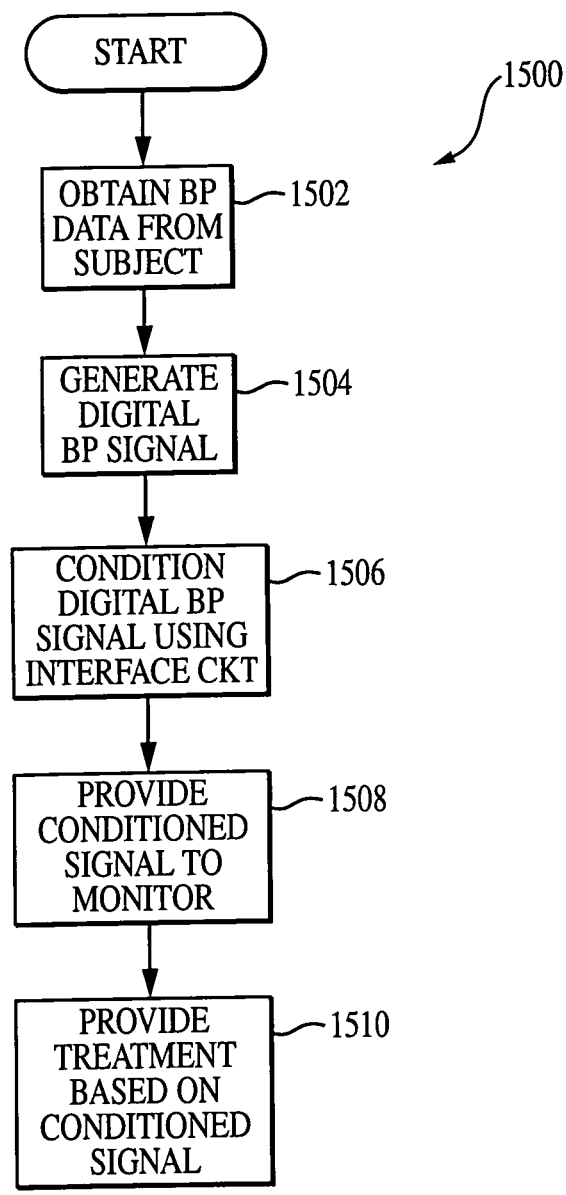
FIG. 15 is a logical flow diagram illustrating one exemplary embodiment of the method of providing treatment to a subject using the aforementioned apparatus and methods.

Referring now to FIG. 15, a method of providing treatment to a subject using the aforementioned hemodynamic assessment and interface circuit apparatus is described in detail. It will be recognized that while the following method of treatment is cast in terms of arterial blood pressure monitoring for a living subject, parameters other than blood pressure may be monitored using the methods of the invention, and other courses of therapy or treatment provided.

As illustrated in FIG. 15, the first step 1502 of the method 1500 comprises obtaining data from the subject using a sensing device such as the NIPBM described previously herein. The data obtained from the subject comprises hemodynamic data (e.g., pressure, velocity, kinetic energy) obtained from the subject, such as from the radial artery. A digital domain signal is next generated in step 1504 based at least in part on the data obtained in step 1502; blood pressure signal generation is described explicitly in the aforementioned co-pending U.S. patent applications previously incorporated herein. Next, in step 1506, the digital domain signal is conditioned using the interface circuit 800, 900, 1100 to produce an analog signal. As previously described herein, the interface circuitry, inter alia, applies a transfer function to the data after conversion from the digital domain to the analog domain, so as to substantially replicate the output which would be provided by a desired "target" device, in this case a passive resistor bridge circuit of the type well known in the art.

The conditioned analog signal is then provided to the patient monitoring device in step 1508, the latter producing a representation of the desired parameter in real time. Such representation may comprise, for example, calibrated displays the systolic, diastolic, and mean pressure waveforms obtained from the subject, or alternatively other representations such as digital values of the systolic, diastolic, and mean pressures. Lastly, in step 1510, treatment is provided to the living subject based on the parametric representation of step 1508. The caregiver may prescribe a course of treatment based on the displayed representation, such as the administration pharmaceuticals, or additional monitoring. Alternatively, such calibrated measurements may be collected over an extended period of time and analyzed for long term trends in the condition or response of the circulatory system of the subject. As yet another alternative, the treatment may be automatically provided based on the signals output to the patient monitor (or derivations thereof), for example such as sounding an alarm to draw attention to the rapidly falling mean blood pressure level of the patient, or adjusting parameters associated with the NIBPM or other monitoring devices being used on the subject.

It will be appreciated that while certain aspects of the invention have been described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:
1. Apparatus, comprising:
   sensing apparatus adapted to sense at least one waveform, and generate a binary digital representation related thereto;
   interface circuit adapted to mimic a passive bridge device and that substantially separates said sensed at least one waveform from an excitation signal, where said excitation signal is provided from a patient monitor; and
   said interface circuit operatively coupled to said sensing apparatus, said interface circuit adapted to:
      when said excitation signal is not present, generate a monitor disconnect signal;
      otherwise:
         apply a transfer function to said binary digital representation;
         generate at least one analog output signal for transmission to a patient monitor device that is based at least in part on:
            1. said binary digital representation of said sensed at least one waveform, 2. said excitation signal provided to said interface circuit from said patient monitor, and 3. said applied transfer function
               where said at least one analog output signal is substantially equivalent to an output signal produced by said passive bridge device placed under a comparable excitation signal and a comparable measured pressure waveform; and
            wherein said excitation signal is substantially equivalent to a signal used to energize circuit elements in said passive bridge device.

2. The apparatus of claim 1, wherein said sensing apparatus comprises a non-invasive blood pressure monitor.

3. The apparatus of claim 2, wherein said binary digital representation comprises data representative of blood pressure obtained from a blood vessel of a living subject.

4. The apparatus of claim 3, wherein said binary digital representation is derived at least in part by calculating time frequency distributions for said at least one waveform.

5. The apparatus of claim 3, wherein said binary digital representation is derived by said sensing apparatus comprising:
   (i) logic configured to measure a first parameter from said blood vessel;
   (ii) logic configured to cause compression of said blood vessel;
   (iii) logic configured to measure a second parameter from said blood vessel when said blood vessel is compressed;
   (iv) logic configured to derive a calibration function based at least in part on said second parameter; and
   (v) logic configured to calibrate said first parameter using said calibration function.

6. The apparatus of claim 5, wherein said first parameter comprises pressure within said blood vessel, and said second parameter comprises blood flow kinetic energy.

7. The apparatus of claim 1, further comprising a wireless communications interface, said wireless interface being adapted to communicate data between said sensing apparatus and said interface circuit.

8. The apparatus of claim 1, further comprising a wireless communications interface, said wireless interface being adapted to communicate data between said apparatus and a monitoring device.

9. The apparatus of claim 7, wherein said wireless interface utilizes radio frequency energy to communicate said data.

10. The apparatus of claim 9, wherein said radio frequency energy is disposed substantially within an Industrial Scientific Medical (ISM) band.

11. The apparatus of claim 9, wherein said wireless interface comprises a spread spectrum device.

12. Apparatus for processing a blood pressure waveform obtained from a non-invasive blood pressure sensing device, comprising:
   first apparatus configured to receive a digital representation of said blood pressure waveform;
   Interface circuit adapted to mimic a passive bridge device and that substantially separates said sensed at least one waveform from an excitation signal, where said excitation signal is provided from a patient monitor;
   second apparatus configured to generate at least one analog output signal based at least in part on: said digital representation of said blood pressure waveform, an applied transfer function, and said excitation signal configured for use as reference input to said applied transfer function, said excitation signal is substantially equivalent to a signal utilized to excite circuit elements in said passive bridge device, and said at least one analog signal is substantially equivalent to an output signal produced by said passive bridge device placed under comparable excitation signal and a comparable measured pressure waveform; and said interface circuit configured to provide said at least one analog output signal to said monitor;

wherein said second apparatus is further configured to function with a plurality of types of excitation signal types corresponding to a plurality of types of monitors, said plurality comprising: (i) constant voltage drive of either polarity, and (ii) constant current drive of either direction.

13. The apparatus of claim 12, wherein said plurality of types of excitation signal types received from said monitor further comprises (iii) any AC voltage or current drive of any waveshape, duty cycle, and DC offset with a frequency of 1 KHz to 10 KHz.

14. The apparatus of claim 12, wherein said transfer function comprises a transfer function which substantially replicates that of a passive bridge transducer.

15. A method for processing a blood pressure waveform obtained from a non-invasive blood pressure sensing device, said method comprising:

sensing at least one waveform via at least one sensing apparatus;

generating a binary digital representation related to said at least one sensed waveform via at least one interface circuit operatively coupled to said at least one sensing apparatus;

where said digital representation is substantially separated from an excitation signal by said at least one interface circuit adapted to mimic a passive bridge device, said excitation signal provided from a patient monitor device;

applying a transfer function to said digital representation at said at least one interface circuit; and generating at least one analog output signal for transmission to said patient monitor device that is based at least in part on: said digital representation of said sensed waveform, said applied transfer function, and an excitation signal provided to said at least one interface circuit, said at least one analog output signal being substantially similar to an output signal produced by said passive bridge device placed under comparable excitation signal and a comparable measured pressure waveform inputs;

where said excitation signal is substantially equivalent to a signal used to energize circuit elements in said passive bridge device; and when said excitation signal is not present, said interface circuit generates a monitor disconnect signal.

* * * * *